(12) United States Patent
Efcavitch et al.

(10) Patent No.: US 10,774,316 B2
(45) Date of Patent: Sep. 15, 2020

(54) MODIFIED TEMPLATE-INDEPENDENT ENZYMES FOR POLYDEOXYNUCLEOTIDE SYNTHESIS

(71) Applicant: Molecular Assemblies, Inc., San Diego, CA (US)

(72) Inventors: J. William Efcavitch, San Carlos, CA (US); Julie L. Tubbs, San Diego, CA (US); Prem Sinha, San Deigo, CA (US); Boguslaw Stec, San Diego, CA (US)

(73) Assignee: Molecular Assemblies, Inc., San Diego, CA (US)

( * ) Notice: Subject to any disclaimer, the term of this patent is extended or adjusted under 35 U.S.C. 154(b) by 54 days.

(21) Appl. No.: 16/165,465

(22) Filed: Oct. 19, 2018

(65) Prior Publication Data

US 2020/0190491 A1    Jun. 18, 2020

Related U.S. Application Data

(63) Continuation-in-part of application No. 16/113,757, filed on Aug. 27, 2018, which is a continuation of application No. 14/918,212, filed on Oct. 20, 2015, now Pat. No. 10,059,929.

(60) Provisional application No. 62/065,976, filed on Oct. 20, 2014.

(51) Int. Cl.
*C12N 9/12* (2006.01)
*C12P 19/34* (2006.01)

(52) U.S. Cl.
CPC ............ *C12N 9/1264* (2013.01); *C12P 19/34* (2013.01); *C12Y 207/07031* (2013.01)

(58) Field of Classification Search
None
See application file for complete search history.

(56) References Cited

U.S. PATENT DOCUMENTS

| 8,808,989 | B1 | 8/2014 | Efcavitch et al. |
| 2004/0043396 | A1 | 3/2004 | Mueller et al. |
| 2011/0081647 | A1 | 4/2011 | Siddiqi et al. |
| 2012/0202196 | A1 | 8/2012 | Balasubramanian et al. |
| 2014/0141414 | A1 | 5/2014 | Liu et al. |
| 2016/0108382 | A1 | 4/2016 | Efcavitch et al. |

FOREIGN PATENT DOCUMENTS

| WO | 2016028802 A1 | 2/2016 |
| WO | 2016128731 A1 | 8/2016 |
| WO | 2018102818 A1 | 6/2018 |

OTHER PUBLICATIONS

Database Uniparc [Online], Jan. 31, 2014, Retrieved from UniProt Database Accession No. UPI0003E329AC (1 Page).
Delarue et al. "Crystal Structures of a Template-Independent DNA Polymerase: Murine Terminal Deoxynucleotidyltransferase," EMBO J. Feb. 1, 2002 (Feb. 1, 2002), vol. 21, pp. 427-439 (13 Pages).
Extended European Search Report dated Mar. 9, 2018 for European Application No. 15851895.1 (7 Pages).
International Search Report and Written Opinion dated Feb. 4, 2020, for International Patent Application No. PCT/U2019/57014, filed Oct. 18, 2019 (9 pages).
International Serach Report and Written Opinion of the International Searching Authority dated Feb. 9, 2016 for International Application No. PCT/US2015/056467 (13 Pages).
Morrison, Kim L et al., "Combinatorial Alanine-Scanning", Current Opinion in Chemical Biology, vol. 5, pp. 302-307 (6 Pages).
Yang et al. "Mutational Analysis of Residues in the Nucleotide Binding Domain of Human Terminal Deoxynucleotidyl Transerase," J Biol Chem. Apr. 22, 1994 (Apr. 22, 1994), vol. 269, pp. 11859118-68 (10 Pages).
Yang, Baoli et al., "Mutational Analysis of Residues in the Nucleotide Binding Domain of Human Terminal Deoxynucleotidyl Transferase", Journal of Biological Chemistry, Apr. 22, 1994, pp. 11859-11868 (10 Pages).

*Primary Examiner* — Anand U Desai
(74) *Attorney, Agent, or Firm* — Brown Rudnick LLP; Thomas C. Meyers

(57) ABSTRACT

The invention includes methods for identifying polymerases, such as modified terminal nucleotidyl transferases (TdT), that are capable of binding nucleotides comprising removable 3'-O-blocking moieties to a nucleic acid initiator, without the use of a template. The invention further includes the identified polymerases, and methods of using the polymerases for de novo synthesis of predetermined oligonucleotide sequences.

20 Claims, 12 Drawing Sheets

Specification includes a Sequence Listing.

| Mutant (Crystal Numbering) | GGFRR | TGSR | 3'-AzM-dTTP | 3'-AzM-dATP | 3'-AzM-dGTP | 3'-Aminoxy-dTTP |
|---|---|---|---|---|---|---|
| E180D+W450H | N | N | + | ≤0 | ≤0 | + |
| M192E | N | N | + | + | n/a | + |
| E180K | N | N | + | + | + | + |
| E180K+R454A | N | Y | + | + | n/a | + |
| R454K | N | Y | + | + | n/a | + |
| M192K | N | N | + | + | + | + |
| M192K+E180K | N | N | + | + | + | + |
| Q455I | N | N | + | + | n/a | + |
| M192W | N | N | n/a | + | n/a | n/a |

| Mutant (Crystal Numbering) | GGFRR | TGSR | 3'-AzM-dATP | 3'-MOM-dTTP | 3'-MTM-dCTP |
|---|---|---|---|---|---|
| E180R | N | N | ≤0 | ≤0 | + |
| E180L | N | N | ≤0 | ≤0 | + |
| M192R | N | N | ≤0 | ≤0 | + |
| E180K+R454I | N | Y | ≤0 | ≤0 | + |
| E180D+M192E | N | N | ≤0 | ≤0 | + |
| E180D+M192E+R454T | N | Y | ≤0 | ≤0 | + |
| E180K+W450H | N | N | ≤0 | + | ≤0 |

| Mutant (Crystal Numbering) | GGFRR | TGSR | 3'-AzM-dTTP | 3'-AzM-dATP | 3'-AzM-dGTP | 3'-Aminoxy-dTTP | 3'-MOM-dTTP | 3'-MTM-dCTP | 3'-Aminoxy-dATP | 3'-Aminoxy-dGTP | 3'-Aminoxy-dCTP | 3'-O-methyl-dATP | 3'-O-methyl-dGTP | 3'-O-methyl-dCTP |
|---|---|---|---|---|---|---|---|---|---|---|---|---|---|---|
| N474R | N | N | ≤0 | + | n/a | + | ≤0 | ≤0 | + | + | + | + | + | ≤0 |
| R461V | N | N | + | ≤0 | n/a | + | + | + | + | + | + | + | + | + |

FIG. 5

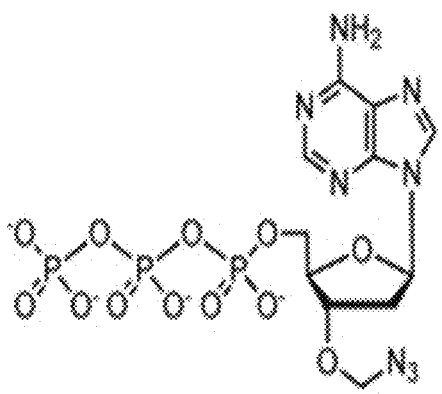
3'-O-N₃-dATP
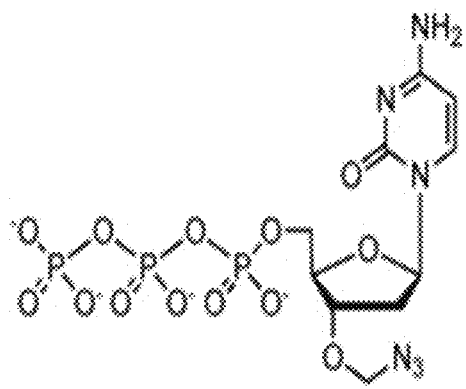
3'-O-N₃-dCTP
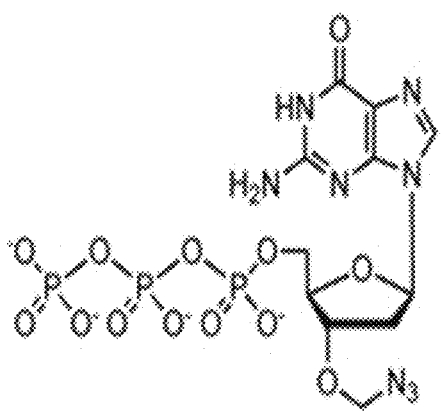
3'-O-N₃-dGTP
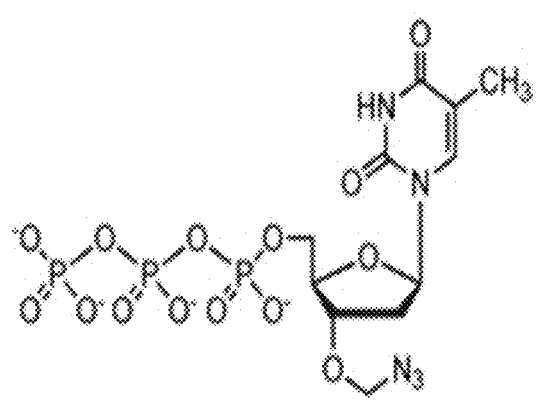
3'-O-N₃-dTTP
FIG. 6

SEQUENCE LISTING

```
<160> NUMBER OF SEQ ID NOS: 9

<210> SEQ ID NO 1
<211> LENGTH: 520
<212> TYPE: PRT
<213> ORGANISM: Bos taurus

<400> SEQUENCE: 1

Met Ala Gln Gln Arg Gln His Gln Arg Leu Pro Met Asp Pro Leu Cys
1               5                   10                  15

Thr Ala Ser Ser Gly Pro Arg Lys Lys Arg Pro Arg Gln Val Gly Ala
                20                  25                  30

Ser Met Ala Ser Pro Pro His Asp Ile Lys Phe Gln Asn Leu Val Leu
            35                  40                  45

Phe Ile Leu Glu Lys Lys Met Gly Thr Thr Arg Arg Asn Phe Leu Met
        50                  55                  60

Glu Leu Ala Arg Arg Lys Gly Phe Arg Val Glu Asn Glu Leu Ser Asp
65                  70                  75                  80

Ser Val Thr His Ile Val Ala Glu Asn Asn Ser Gly Ser Glu Val Leu
                85                  90                  95

Glu Trp Leu Gln Val Gln Asn Ile Arg Ala Ser Ser Gln Leu Glu Leu
            100                 105                 110

Leu Asp Val Ser Trp Leu Ile Glu Ser Met Gly Ala Gly Lys Pro Val
        115                 120                 125

Glu Ile Thr Gly Lys His Gln Leu Val Val Arg Thr Asp Tyr Ser Ala
    130                 135                 140

Thr Pro Asn Pro Gly Phe Gln Lys Thr Pro Pro Leu Ala Val Lys Lys
145                 150                 155                 160

Ile Ser Gln Tyr Ala Cys Gln Arg Lys Thr Thr Leu Asn Asn Tyr Asn
                165                 170                 175

His Ile Phe Thr Asp Ala Phe Glu Ile Leu Ala Glu Asn Ser Glu Phe
            180                 185                 190

Lys Glu Asn Glu Val Ser Tyr Val Thr Phe Met Arg Ala Ala Ser Val
        195                 200                 205

Leu Lys Ser Leu Pro Phe Thr Ile Ile Ser Met Lys Asp Thr Glu Gly
    210                 215                 220

Ile Pro Cys Leu Gly Asp Lys Val Lys Cys Ile Ile Glu Glu Ile Ile
225                 230                 235                 240

Glu Asp Gly Glu Ser Ser Glu Val Lys Ala Val Leu Asn Asp Glu Arg
                245                 250                 255

Tyr Gln Ser Phe Lys Leu Phe Thr Ser Val Phe Gly Val Gly Leu Lys
            260                 265                 270

Thr Ser Glu Lys Trp Phe Arg Met Gly Phe Arg Ser Leu Ser Lys Ile
        275                 280                 285
```

```
Met Ser Asp Lys Thr Leu Lys Phe Thr Lys Met Gln Lys Ala Gly Phe
    290                 295                 300
Leu Tyr Tyr Glu Asp Leu Val Ser Cys Val Thr Arg Ala Glu Ala Glu
305                 310                 315                 320
Ala Val Gly Val Leu Val Lys Glu Ala Val Trp Ala Phe Leu Pro Asp
                    325                 330                 335
Ala Phe Val Thr Met Thr Gly Gly Phe Arg Arg Gly Lys Lys Ile Gly
                340                 345                 350
His Asp Val Asp Phe Leu Ile Thr Ser Pro Gly Ser Ala Glu Asp Glu
                355                 360                 365
Glu Gln Leu Leu Pro Lys Val Ile Asn Leu Trp Glu Lys Lys Gly Leu
370                 375                 380
Leu Leu Tyr Tyr Asp Leu Val Glu Ser Thr Phe Glu Lys Phe Lys Leu
385                 390                 395                 400
Pro Ser Arg Gln Val Asp Thr Leu Asp His Phe Gln Lys Cys Phe Leu
                    405                 410                 415
Ile Leu Lys Leu His His Gln Arg Val Asp Ser Ser Lys Ser Asn Gln
                420                 425                 430
Gln Glu Gly Lys Thr Trp Lys Ala Ile Arg Val Asp Leu Val Met Cys
                435                 440                 445
Pro Tyr Glu Asn Arg Ala Phe Ala Leu Leu Gly Trp Thr Gly Ser Arg
        450                 455                 460
Gln Phe Glu Arg Asp Ile Arg Arg Tyr Ala Thr His Glu Arg Lys Met
465                 470                 475                 480
Met Leu Asp Asn His Ala Leu Tyr Asp Lys Thr Lys Arg Val Phe Leu
                    485                 490                 495
Lys Ala Glu Ser Glu Glu Ile Phe Ala His Leu Gly Leu Asp Tyr
                500                 505                 510
Ile Glu Pro Trp Glu Arg Asn Ala
        515                 520

<210> SEQ ID NO 2
<211> LENGTH: 1923
<212> TYPE: DNA
<213> ORGANISM: Bos taurus

<400> SEQUENCE: 2
ctcttctgga gataccactt gatggcacag cagaggcagc atcagcgtct tcccatggat    60
ccgctgtgca gcctcctc aggccctcgg aagaagagac ccaggcaggt gggtgcctca    120
atggcctccc ctcctcatga catcaagttt caaaatttgg tcctcttcat tttggagaag    180
aaaatgggaa ccacccgcag aaacttcctc atggagctgg ctcgaaggaa aggtttcagg    240
gttgaaaatg agctcagtga ttctgtcacc cacattgtag cagaaaacaa ctctggttca    300
gaggttctcg agtggcttca ggtacagaac ataagagcca gctcgcagct agaactcctt    360
gatgtctcct ggctgatcga agtatggga gcaggaaaac cagtggagat acaggaaaa    420
caccagcttg ttgtgagaac agactattca gctaccccaa acccaggctt ccagaagact    480
ccaccacttg ctgtaaaaaa gatctcccag tacgcgtgtc aaagaaaaac cactttgaac    540
aactataacc acatattcac ggatgccttt gagatactgg ctgaaaattc tgagtttaaa    600
gaaaatgaag tctcttatgt gacatttatg agagcagctt ctgtacttaa atctctgcca    660
ttcacaatca tcagtatgaa ggatacagaa ggaattccct gcctggggga caaggtgaag    720
tgtatcatag aggaaattat tgaagatgga gaaagttctg aagttaaagc tgtgttaaat    780
```

-continued

```
gatgaacgat atcagtcctt caaactcttt acttctgttt ttggagtggg actgaagaca    840
tctgagaaat ggttcaggat ggggttcaga tctctgagta aaataatgtc agacaaaacc    900
ctgaaattca caaaaatgca gaaagcagga tttctctatt atgaagacct tgtcagctgc    960
gtgaccaggg ccgaagcaga ggcggttggc gtgctggtta agaggctgt gtgggcattt    1020
ctgccggatg cctttgtcac catgacagga ggattccgca ggggtaagaa gattgggcat    1080
gatgtagatt ttttaattac cagcccagga tcagcagagg atgaagagca acttttgcct    1140
aaagtgataa actatgggga aaaaaaggga ttacttttat attatgacct tgtggagtca    1200
acatttgaaa agttcaagtt gccaagcagg caggtggata ctttagatca ttttcaaaaa    1260
tgctttctga ttttaaaatt gcaccatcag agagtagaca gtagcaagtc caaccagcag    1320
gaaggaaaga cctggaaggc catccgtgtg gacctggtta tgtgcccta cgagaaccgt    1380
gcctttgccc tgctaggctg gactggctcc cggcagtttg agagagacat ccggcgctat    1440
gccacacacg agcggaagat gatgctggat aaccacgctt tatatgacaa gaccaagagg    1500
gtatttctca aagcggaaag tgaagaagaa atctttgcac atctgggatt ggactacatt    1560
gaaccatggg aaagaaatgc ttaggagaaa gctgtcaact ttttctttt ctgttctttt    1620
tttcaggtta gacaaattat gcttcatatt ataatgaaag atgccttagt caagtttggg    1680
attctttaca ttttaccaag atgtagattg cttctagaaa taagtagttt tggaaacgtg    1740
atcaggcacc ccctgggtta tgctctggca agccatttgc aggactgatg tgtagaactc    1800
gcaatgcatt ttccatagaa acagtgttgg aattggtggc tcatttccag ggaagttcat    1860
caaagcccac tttgcccaca gtgtagctga atactgtat acttgccaat aaaaatagga    1920
aac                                                                  1923
```

<210> SEQ ID NO 3
<211> LENGTH: 392
<212> TYPE: PRT
<213> ORGANISM: Bos taurus

<400> SEQUENCE: 3

```
Met Arg Gly Ser His His His His His His Arg Thr Asp Tyr Ser Ala
1               5                   10                  15

Thr Pro Asn Pro Gly Phe Gln Lys Thr Pro Leu Ala Val Lys Lys
            20                  25                  30

Ile Ser Gln Tyr Ala Cys Gln Arg Lys Thr Thr Leu Asn Asn Tyr Asn
        35                  40                  45

His Ile Asp Ala Phe Glu Ile Leu Ala Glu Asn Ser Glu Phe Lys Glu
    50                  55                  60

Asn Glu Val Ser Tyr Val Thr Phe Met Arg Ala Ala Ser Val Leu Lys
65                  70                  75                  80

Ser Leu Pro Phe Thr Ile Ile Ser Met Lys Asp Thr Phe Thr Glu Gly
                85                  90                  95

Ile Pro Cys Leu Gly Asp Lys Val Lys Cys Ile Glu Glu Ile Ile
            100                 105                 110

Glu Asp Gly Glu Ser Ser Glu Val Lys Ala Val Leu Asn Asp Glu Arg
        115                 120                 125

Tyr Gln Ser Phe Lys Leu Ser Val Phe Gly Val Gly Leu Lys Thr Ser
    130                 135                 140

Glu Lys Trp Phe Arg Met Gly Phe Thr Phe Arg Ser Leu Ser Lys Ile
145                 150                 155                 160

Met Ser Asp Lys Thr Leu Lys Lys Met Gln Lys Ala Gly Phe Leu Tyr
```

```
                    165                 170                 175
Tyr Glu Asp Leu Val Ser Cys Val Thr Arg Ala Glu Ala Glu Ala Val
                180                 185                 190
Gly Val Leu Val Lys Glu Ala Val Trp Ala Phe Leu Pro Asp Ala Phe
            195                 200                 205
Val Thr Met Thr Gly Gly Phe Arg Arg Gly Lys Lys Ile Gly His Asp
        210                 215                 220
Val Asp Phe Leu Ile Thr Ser Pro Gly Ser Ala Glu Asp Glu Glu Gln
225                 230                 235                 240
Leu Leu Pro Lys Val Ile Asn Leu Trp Glu Lys Lys Gly Leu Leu Leu
                245                 250                 255
Tyr Tyr Asp Leu Val Glu Ser Thr Phe Glu Lys Phe Lys Phe Thr Leu
            260                 265                 270
Pro Ser Arg Gln Val Asp Thr Leu Asp His Phe Gln Lys Cys Phe Leu
        275                 280                 285
Ile Leu Lys Leu His His Gln Arg Val Asp Ser Ser Lys Ser Asn Gln
    290                 295                 300
Gln Glu Gly Lys Thr Trp Lys Ala Ile Arg Val Asp Leu Val Met Cys
305                 310                 315                 320
Pro Tyr Glu Asn Arg Ala Phe Ala Leu Leu Gly Trp Thr Gly Ser Arg
                325                 330                 335
Gln Phe Glu Arg Asp Ile Arg Arg Tyr Ala Thr His Glu Arg Lys Met
            340                 345                 350
Met Leu Asp Asn His Ala Leu Tyr Asp Lys Thr Lys Arg Val Phe Leu
        355                 360                 365
Lys Ala Glu Ser Glu Glu Ile Phe Ala His Leu Gly Leu Asp Tyr
    370                 375                 380
Ile Glu Pro Trp Glu Arg Asn Ala
385                 390

<210> SEQ ID NO 4
<211> LENGTH: 1187
<212> TYPE: DNA
<213> ORGANISM: Bos taurus

<400> SEQUENCE: 4
atgagaggat cgcatcacca tcaccatcac agaacagact attcagctac cccaaaccca    60
ggcttccaga agactccacc acttgctgta aaaaagatct cccagtacgc gtgtcaaaga   120
aaaaccactt tgaacaacta taaccacata ttcacggatg cctttgagat actggctgaa   180
aattctgagt ttaaagaaaa tgaagtctct tatgtgacat ttatgagagc agcttctgta   240
cttaaatctc tgccattcac aatcatcagt atgaaggata cagaaggaat tccctgcctg   300
ggggacaagg tgaagtgtat catagaggaa attattgaag atggagaaag ttctgaagtt   360
aaagctgtgt taaatgatga acgatatcag tccttcaaac tctttacttc tgttttttgga   420
gtgggactga agacatctga gaatggttca aggatggggt tcagatctct gagtaaaata   480
atgtcagaca aaaccctgaa attcacaaaa atgcagaaag caggatttct ctattatgaa   540
gaccttgtca gctgcgtgac cagggccgaa gcagaggcgg ttggcgtgct ggttaaagag   600
gctgtgtggg catttctgcc ggatgccttt gtcaccatga caggaggatt ccgcagggt    660
aagaagattg gcatgatgt agatttttta attaccagcc caggatcagc agaggatgaa   720
gagcaacttt tgcctaaagt gataaactta tgggaaaaaa aggattact tttatattat   780
gaccttgtgg agtcaacatt tgaaaagttc aagttgccaa gcaggcaggt ggatacttta   840
```

```
gatcattttc aaaaatgctt tctgattta aaattgcacc atcagagagt agacagtagc      900
aagtccaacc agcaggaagg aaagacctgg aaggccatcc gtgtggacct ggttatgtgc      960
ccctacgaga accgtgcctt tgccctgcta ggctggactg gctcccggca gtttgagaga     1020
gacatccggc gctatgccac acacgagcgg aagatgatgc tggataacca cgctttatat     1080
gacaagacca gagggtatt tctcaaagcg gaaagtgaag aagaaatctt tgcacatctg     1140
ggattggact acattgaacc atgggaaaga aatgcttaag cttgcgc                  1187
```

<210> SEQ ID NO 5
<211> LENGTH: 379
<212> TYPE: PRT
<213> ORGANISM: Bos taurus

<400> SEQUENCE: 5

```
Met Arg Gly Ser His His His His His Lys Thr Pro Pro Leu Ala
 1               5                  10                  15

Val Lys Lys Ile Ser Gln Tyr Ala Cys Gln Arg Lys Thr Thr Leu Asn
            20                  25                  30

Asn Tyr Asn His Ile Asp Ala Phe Glu Ile Leu Ala Glu Asn Ser Glu
        35                  40                  45

Phe Lys Glu Asn Glu Val Ser Tyr Val Thr Phe Met Arg Ala Ala Ser
    50                  55                  60

Val Leu Lys Ser Leu Pro Phe Thr Ile Ile Ser Met Lys Asp Thr Phe
65                  70                  75                  80

Thr Glu Gly Ile Pro Cys Leu Gly Asp Lys Val Lys Cys Ile Ile Glu
                85                  90                  95

Glu Ile Ile Glu Asp Gly Glu Ser Ser Glu Val Lys Ala Val Leu Asn
            100                 105                 110

Asp Glu Arg Tyr Gln Ser Phe Lys Leu Ser Val Phe Gly Val Gly Leu
        115                 120                 125

Lys Thr Ser Glu Lys Trp Phe Arg Met Gly Phe Thr Phe Arg Ser Leu
    130                 135                 140

Ser Lys Ile Met Ser Asp Lys Thr Leu Lys Lys Met Gln Lys Ala Gly
145                 150                 155                 160

Phe Leu Tyr Tyr Glu Asp Leu Val Ser Cys Val Thr Arg Ala Glu Ala
                165                 170                 175

Glu Ala Val Gly Val Leu Val Lys Glu Ala Val Trp Ala Phe Leu Pro
            180                 185                 190

Asp Ala Phe Val Thr Met Thr Gly Gly Phe Arg Arg Gly Lys Lys Ile
        195                 200                 205

Gly His Asp Val Asp Phe Leu Ile Thr Ser Pro Gly Ser Ala Glu Asp
    210                 215                 220

Glu Glu Gln Leu Leu Pro Lys Val Ile Asn Leu Trp Glu Lys Lys Gly
225                 230                 235                 240

Leu Leu Leu Tyr Tyr Asp Leu Val Glu Ser Thr Phe Glu Lys Phe Lys
                245                 250                 255

Phe Thr Leu Pro Ser Arg Gln Val Asp Thr Leu Asp His Phe Gln Lys
            260                 265                 270

Cys Phe Leu Ile Leu Lys Leu His His Gln Arg Val Asp Ser Ser Lys
        275                 280                 285

Ser Asn Gln Gln Glu Gly Lys Thr Trp Lys Ala Ile Arg Val Asp Leu
    290                 295                 300

Val Met Cys Pro Tyr Glu Asn Arg Ala Phe Ala Leu Leu Gly Trp Thr
```

```
                305                 310                 315                 320
Gly Ser Arg Gln Phe Glu Arg Asp Ile Arg Arg Tyr Ala Thr His Glu
                    325                 330                 335
Arg Lys Met Met Leu Asp Asn His Ala Leu Tyr Asp Lys Thr Lys Arg
                340                 345                 350
Val Phe Leu Lys Ala Glu Ser Glu Glu Ile Phe Ala His Leu Gly
                355                 360                 365
Leu Asp Tyr Ile Glu Pro Trp Glu Arg Asn Ala
            370                 375

<210> SEQ ID NO 6
<211> LENGTH: 1148
<212> TYPE: DNA
<213> ORGANISM: Bos taurus

<400> SEQUENCE: 6
atgagaggat cgcatcacca tcaccatcac aagactccac cacttgctgt aaaaaagatc      60
tcccagtacg cgtgtcaaag aaaaaccact ttgaacaact ataaccacat attcacggat     120
gcctttgaga tactggctga aaattctgag tttaaagaaa atgaagtctc ttatgtgaca     180
tttatgagag cagcttctgt acttaaatct ctgccattca caatcatcag tatgaaggat     240
acagaaggaa ttccctgcct gggggacaag gtgaagtgta tcatagagga attattgaa      300
gatggagaaa gttctgaagt taaagctgtg ttaaatgatg aacgatatca gtccttcaaa     360
ctctttactt ctgttttgg agtgggactg aagacatctg agaaatggtt caggatgggg      420
ttcagatctc tgagtaaaat aatgtcagac aaaaccctga attcacaaa atgcagaaa       480
gcaggatttc tctattatga agaccttgtc agctgcgtga ccagggccga agcagaggcg     540
gttggcgtgc tggttaaaga ggctgtgtgg gcatttctgc cggatgcctt tgtcaccatg     600
acaggaggat tccgcagggg taagaagatt gggcatgatg tagattttttt aattaccagc   660
ccaggatcag cagaggatga agagcaactt ttgcctaaag tgataaactt atgggaaaaa    720
aagggattac ttttatatta tgaccttgtg gagtcaacat ttgaaaagtt caagttgcca    780
agcaggcagg tggatacttt agatcatttt caaaaatgct ttctgatttt aaaattgcac    840
catcagagag tagacagtag caagtccaac cagcaggaag gaaagacctg gaaggccatc    900
cgtgtggacc tggttatgtg cccctacgag aaccgtgcct tgccctgct aggctggact    960
ggctcccggc agtttgagag agacatccgg cgctatgcca cacacgagcg gaagatgatg   1020
ctggataacc acgctttata tgacaagacc aagagggtat ttctcaaagc ggaaagtgaa   1080
gaagaaatct ttgcacatct gggattggac tacattgaac catgggaaag aaatgcttaa   1140
gcttgcgc                                                            1148

<210> SEQ ID NO 7
<211> LENGTH: 370
<212> TYPE: PRT
<213> ORGANISM: Bos taurus

<400> SEQUENCE: 7

Met Arg Gly Ser His His His His His His Ile Ser Gln Tyr Ala Cys
1                5                  10                  15
Gln Arg Lys Thr Thr Leu Asn Asn Tyr Asn His Ile Asp Ala Phe Glu
                20                  25                  30
Ile Leu Ala Glu Asn Ser Glu Phe Lys Glu Asn Glu Val Ser Tyr Val
            35                  40                  45
```

```
Thr Phe Met Arg Ala Ala Ser Val Leu Lys Ser Leu Pro Phe Thr Ile
         50                  55                  60
Ile Ser Met Lys Asp Thr Phe Thr Glu Gly Ile Pro Cys Leu Gly Asp
 65                  70                  75                  80
Lys Val Lys Cys Ile Ile Glu Glu Ile Ile Glu Asp Gly Glu Ser Ser
                 85                  90                  95
Glu Val Lys Ala Val Leu Asn Asp Glu Arg Tyr Gln Ser Phe Lys Leu
            100                 105                 110
Ser Val Phe Gly Val Gly Leu Lys Thr Ser Glu Lys Trp Phe Arg Met
            115                 120                 125
Gly Phe Thr Phe Arg Ser Leu Ser Lys Ile Met Ser Asp Lys Thr Leu
130                 135                 140
Lys Lys Met Gln Lys Ala Gly Phe Leu Tyr Tyr Glu Asp Leu Val Ser
145                 150                 155                 160
Cys Val Thr Arg Ala Glu Ala Glu Ala Val Gly Val Leu Val Lys Glu
                165                 170                 175
Ala Val Trp Ala Phe Leu Pro Asp Ala Phe Val Thr Met Thr Gly Gly
            180                 185                 190
Phe Arg Arg Gly Lys Lys Ile Gly His Asp Val Asp Phe Leu Ile Thr
            195                 200                 205
Ser Pro Gly Ser Ala Glu Asp Glu Glu Gln Leu Leu Pro Lys Val Ile
210                 215                 220
Asn Leu Trp Glu Lys Lys Gly Leu Leu Leu Tyr Tyr Asp Leu Val Glu
225                 230                 235                 240
Ser Thr Phe Glu Lys Phe Lys Phe Thr Leu Pro Ser Arg Gln Val Asp
                245                 250                 255
Thr Leu Asp His Phe Gln Lys Cys Phe Leu Ile Leu Lys Leu His His
            260                 265                 270
Gln Arg Val Asp Ser Ser Lys Ser Asn Gln Gln Glu Gly Lys Thr Trp
            275                 280                 285
Lys Ala Ile Arg Val Asp Leu Val Met Cys Pro Tyr Glu Asn Arg Ala
290                 295                 300
Phe Ala Leu Leu Gly Trp Thr Gly Ser Arg Gln Phe Glu Arg Asp Ile
305                 310                 315                 320
Arg Arg Tyr Ala Thr His Glu Arg Lys Met Met Leu Asp Asn His Ala
                325                 330                 335
Leu Tyr Asp Lys Thr Lys Arg Val Phe Leu Lys Ala Glu Ser Glu Glu
            340                 345                 350
Glu Ile Phe Ala His Leu Gly Leu Asp Tyr Ile Glu Pro Trp Glu Arg
            355                 360                 365
Asn Ala
    370

<210> SEQ ID NO 8
<211> LENGTH: 1121
<212> TYPE: DNA
<213> ORGANISM: Bos taurus

<400> SEQUENCE: 8
atgagaggat cgcatcacca tcaccatcac atctcccagt acgcgtgtca agaaaaaacc      60
actttgaaca actataacca catattcacg gatgcctttg agatactggc tgaaaattct     120
gagtttaaag aaaatgaagt ctcttatgtg acatttatga gcagcttc tgtacttaaa      180 tctctgccat tcacaatcat cagtatgaag gatacagaag gaattccctg cctgggggac     240
```

```
aaggtgaagt gtatcataga ggaaattatt gaagatggag aaagttctga agttaaagct      300
gtgttaaatg atgaacgata tcagtccttc aaactcttta cttctgtttt tggagtggga      360
ctgaagacat ctgagaaatg gttcaggatg gggttcagat ctctgagtaa aataatgtca      420
gacaaaaccc tgaaattcac aaaaatgcag aaagcaggat ttctctatta tgaagacctt      480
gtcagctgcg tgaccagggc cgaagcagag gcggttggcg tgctggttaa agaggctgtg      540
tgggcatttc tgccggatgc ctttgtcacc atgacaggag gattccgcag gggtaagaag      600
attgggcatg atgtagattt tttaattacc agcccaggat cagcagagga tgaagagcaa      660
cttttgccta aagtgataaa cttatgggaa aaaaagggat tacttttata ttatgacctt      720
gtggagtcaa catttgaaaa gttcaagttg ccaagcaggc aggtggatac tttagatcat      780
tttcaaaaat gctttctgat tttaaaattg caccatcaga gagtagacag tagcaagtcc      840
aaccagcagg aaggaaagac ctggaaggcc atccgtgtgg acctggttat gtgcccctac      900
gagaaccgtg cctttgccct gctaggctgg actggctccc ggcagtttga gagagacatc      960
cggcgctatg ccacacacga gcggaagatg atgctggata ccacgctttt atatgacaag     1020
accaagaggg tatttctcaa agcggaaagt gaagaagaaa tctttgcaca tctgggattg     1080
gactacattg aaccatggga agaaatgctt aagcttgcg c                         1121
```

<210> SEQ ID NO 9
<211> LENGTH: 510
<212> TYPE: PRT
<213> ORGANISM: Mus musculus

<400> SEQUENCE: 9

```
Met Asp Pro Leu Gln Ala Val His Leu Gly Pro Arg Lys Lys Arg Pro
1               5                   10                  15

Arg Gln Leu Gly Thr Pro Val Ala Ser Thr Pro Tyr Asp Ile Arg Phe
            20                  25                  30

Arg Asp Leu Val Leu Phe Ile Leu Glu Lys Lys Met Gly Thr Thr Arg
        35                  40                  45

Arg Ala Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Leu Gln Asn Ile Lys Ala Ser
                85                  90                  95

Ser Glu Leu Glu Leu Leu Asp Ile Ser Trp Leu Ile Glu Cys Met Gly
            100                 105                 110

Ala Gly Lys Pro Val Glu Met Met Gly Arg His Gln Leu Val Val Asn
        115                 120                 125

Arg Asn Ser Ser Pro Ser Pro Val Pro Gly Ser Gln Asn Val Pro Ala
    130                 135                 140

Pro Ala Val Lys Lys Ile Ser Gln Tyr Ala Cys Gln Arg Arg Thr Thr
145                 150                 155                 160

Leu Asn Asn Tyr Asn Gln Leu Phe Thr Asp Ala Leu Asp Ile Leu Ala
                165                 170                 175

Glu Asn Asp Glu Leu Arg Glu Asn Glu Gly Ser Cys Leu Ala Phe Met
            180                 185                 190

Arg Ala Ser Ser Val Leu Lys Ser Leu Pro Phe Pro Ile Thr Ser Met
        195                 200                 205

Lys Asp Thr Glu Gly Ile Pro Cys Leu Gly Asp Lys Val Lys Ser Ile
    210                 215                 220
```

```
Ile Glu Gly Ile Ile Glu Asp Gly Glu Ser Ser Glu Ala Lys Ala Val
225                 230                 235                 240

Leu Asn Asp Glu Arg Tyr Lys Ser Phe Lys Leu Phe Thr Ser Val Phe
            245                 250                 255

Gly Val Gly Leu Lys Thr Ala Glu Lys Trp Phe Arg Met Gly Phe Arg
        260                 265                 270

Thr Leu Ser Lys Ile Gln Ser Asp Lys Ser Leu Arg Phe Thr Gln Met
    275                 280                 285

Gln Lys Ala Gly Phe Leu Tyr Tyr Glu Asp Leu Val Ser Cys Val Asn
290                 295                 300

Arg Pro Glu Ala Glu Ala Val Ser Met Leu Val Lys Glu Ala Val Val
305                 310                 315                 320

Thr Phe Leu Pro Asp Ala Leu Val Thr Met Thr Gly Gly Phe Arg Arg
                325                 330                 335

Gly Lys Met Thr Gly His Asp Val Asp Phe Leu Ile Thr Ser Pro Glu
            340                 345                 350

Ala Thr Glu Asp Glu Glu Gln Gln Leu Leu His Lys Val Thr Asp Phe
        355                 360                 365

Trp Lys Gln Gln Gly Leu Leu Leu Tyr Cys Asp Ile Leu Glu Ser Thr
    370                 375                 380

Phe Glu Lys Phe Lys Gln Pro Ser Arg Lys Val Asp Ala Leu Asp His
385                 390                 395                 400

Phe Gln Lys Cys Phe Leu Ile Leu Lys Leu Asp His Gly Arg Val His
                405                 410                 415

Ser Glu Lys Ser Gly Gln Gln Glu Gly Lys Gly Trp Lys Ala Ile Arg
            420                 425                 430

Val Asp Leu Val Met Cys Pro Tyr Asp Arg Arg Ala Phe Ala Leu Leu
        435                 440                 445

Gly Trp Thr Gly Ser Arg Gln Phe Glu Arg Asp Leu Arg Arg Tyr Ala
    450                 455                 460

Thr His Glu Arg Lys Met Met Leu Asp Asn His Ala Leu Tyr Asp Arg
465                 470                 475                 480

Thr Lys Arg Val Phe Leu Glu Ala Glu Ser Glu Glu Glu Ile Phe Ala
                485                 490                 495

His Leu Gly Leu Asp Tyr Ile Glu Pro Trp Glu Arg Asn Ala
            500                 505                 510
```

MODIFIED TEMPLATE-INDEPENDENT ENZYMES FOR POLYDEOXYNUCLEOTIDE SYNTHESIS

RELATED APPLICATIONS

This Application is a continuation-in-part of U.S. Non-provisional application Ser. No. 16/113,757, filed Aug. 27, 2018, which is a continuation-in-part of U.S. Non-provisional application Ser. No. 14/918,212, filed Oct. 20, 2015, issued as U.S. Pat. No. 10,059,929 on Aug. 28, 2018, which claims priority to U.S. Provisional Application No. 62/065,976, filed Oct. 20, 2014, the contents of each of which are incorporated by reference herein.

FIELD OF THE INVENTION

The invention relates to modified enzymes for de novo synthesis of polynucleotides with a desired sequence, and without the use of a template. As such, the invention provides the capability to make libraries of polynucleotides of varying sequence and varying length for research, genetic engineering, and gene therapy.

BACKGROUND

Most de novo nucleic acid sequences are synthesized using solid phase phosphoramidite-techniques developed more than 30 years ago. The technique involves the sequential de-protection and synthesis of sequences built from phosphoramidite reagents corresponding to natural (or non-natural) nucleic acid bases. Phosphoramidite nucleic acid synthesis is length-limited, however, in that nucleic acids greater than 200 base pairs (bp) in length experience high rates of breakage and side reactions. Additionally, phosphoramidite synthesis produces toxic by-products, and the disposal of this waste limits the availability of nucleic acid synthesizers, and increases the costs of contract oligo production. (It is estimated that the annual demand for oligonucleotide synthesis is responsible for greater than 300,000 gallons of hazardous chemical waste, including acetonitrile, trichloroacetic acid, toluene, tetrahydrofuran, and pyridine. See LeProust et al., *Nucleic Acids Res.*, vol. 38(8), p. 2522-2540, (2010), incorporated by reference herein in its entirety). Thus, there is a need for more efficient and cost-effective methods for oligonucleotide synthesis.

SUMMARY

The invention discloses modified terminal deoxynucleotidyl transferase (TdT) enzymes that can be used for de novo sequencing of oligonucleotides in the absence of a template. Methods for creating a template-independent polymerase through a combination of computational guidance and saturation mutagenesis, with a subsequent screen to identify functional mutants, are also disclosed. In some embodiments, the modified TdTs will include a mutation in the GGFRR or TGSR motifs, which interact with the nucleotide during synthesis.

Using the resulting enzymes, it will possible to synthesize de novo polynucleotides faster and cheaper. As such, the invention dramatically reduces the overall cost of synthesizing custom nucleic acids. In particular, the methods can be used to create template-independent transferases that can synthesize custom oligos in a stepwise fashion using modified 3' hydroxyl-blocked nucleotides. Because of the terminating group, synthesis pauses with the addition of each new base, whereupon the terminating group is cleaved, leaving a polynucleotide that is essentially identical to a naturally occurring nucleotide (i.e., is recognized by the enzyme as a substrate for further nucleotide incorporation).

The methods and enzymes of the invention represent an important step forward in synthetic biology because the enzymes will allow for aqueous phase, template-independent oligonucleotide synthesis. Such methods represent an improvement over the prior art in that they will greatly reduce the chemical waste produced during oligonucleotide synthesis while allowing for the production of longer polynucleotides. Furthermore, because the methods replace a chemical process with a biological one, costs will be reduced, and the complexity of automated synthetic systems will also be reduced. In an embodiment, a simple five-reagent delivery system can be used to build oligonucleotides in a stepwise fashion and will enable recycling of unused reagents.

BRIEF DESCRIPTION OF THE DRAWINGS

FIG. 5 shows a table of TdT variants that were selected for increased incorporation of selected 3'-O-blocked dNTP analogs as described herein.

FIG. 6 shows exemplary 3'-O-azidomethyl deoxynucleotides that can be used to synthesize custom DNA oligomers using modified TdTs, as described herein.

DESCRIPTION OF THE INVENTION

The invention facilitates the synthesis of polynucleotides, such as DNA, by providing modified enzymes that can be used with nucleic acid analogs. Using the disclosed methods, a modified template-independent terminal deoxynucleotidyl transferase (TdT) is obtained that allows the enzymatically mediated synthesis of de novo oligodeoxynucleotides, thereby enabling their use in routine assembly for gene synthesis. The enzymes of the invention lend themselves to aqueous-based, enzyme-mediated methods of synthesizing polynucleotides of a predetermined sequence on a solid support.

Figure 2:
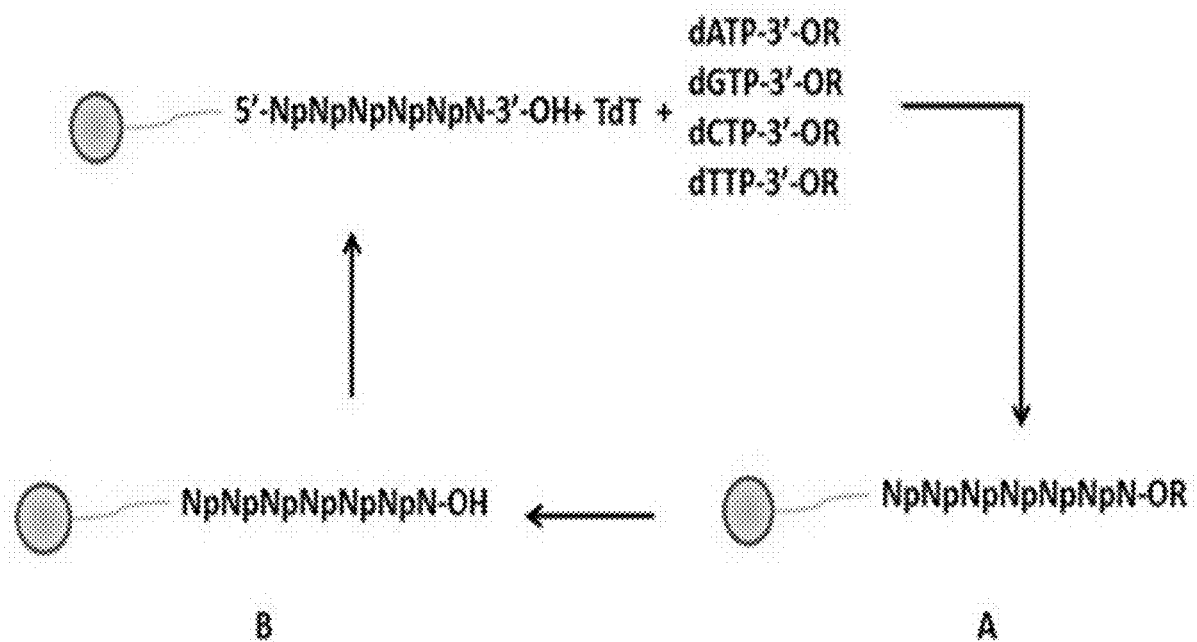
FIG. 2 illustrates an exemplary modified terminal deoxynucleotidyl transferase (TdT) mediated polynucleotide synthesis cycle using a support bound initiator and 3'-O-blocked nucleotide triphosphate including (A) incorporation of a nucleotide analog comprising a cleavable 3'-O-blocking group (indicated by R), and (B) removal of the 3'-O-blocking group thus enabling the next 3'-O-blocked nucleotide analog to be incorporated, wherein N=A, G, C, or T.

The modified enzymes of the invention will allow 3'-O-blocked dNTP analogs to be used in a step-by-step method to extend an initiating nucleic acid into a user defined sequence (see FIG. 2). Furthermore, after each nucleotide extension step, the reactants can be recovered and recycled from the solid support back to the original reagent reservoir. Once that step is complete, the 3'-O-blocking group will be removed, allowing the cycle to start anew. At the conclusion of n cycles of extension-recover-deblock-wash, the full length, single strand polydeoxynucleotide will be cleaved from the solid support and isolated for subsequent use. A variety of 3'-O-blocked deoxynucleotides, may be used, but the choice of specific 3'-O-blocking groups is dictated by: 1) the smallest possible bulk to maximize substrate utilization by TdT and 2) removal of the blocking group with the mildest and preferably aqueous conditions in the shortest period of time.

Cost savings by this approach will be achieved by exploiting the higher yield of final oligonucleotide product at a lower starting scale than currently being used as the existing industry standard (i.e., less than 1 nanomole). Future adaptation of this enzymatic approach to array based formats will allow even further and more dramatic reductions in the cost of synthesis of long oligonucleotides achievable by highly parallel synthesis. Furthermore, the enzymatic synthesis process that we propose uses only aqueous based chemistries like buffers and salts, thus greatly reducing the environmental burden of the organic waste generated by the existing phosphoramidite method.

Figure 1:
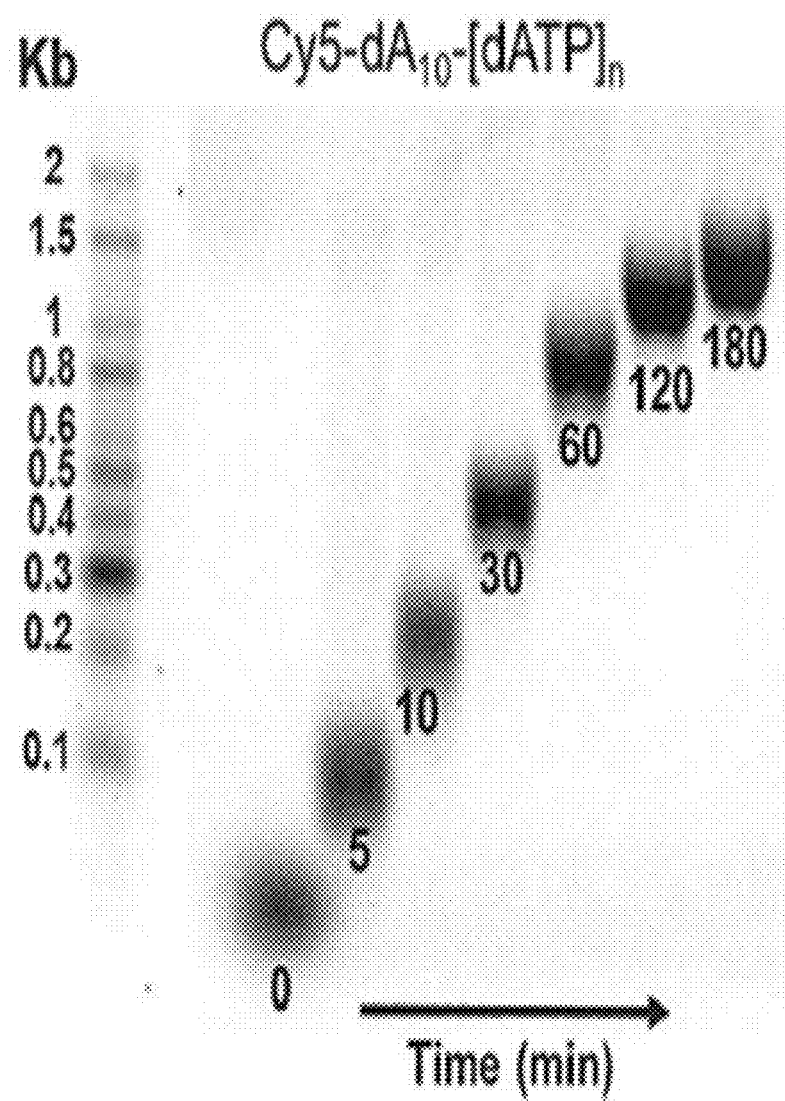
FIG. 1 shows an agarose gel of a solution phase polymerization reaction composed of terminal deoxynucleotidyl transferase (TdT), deoxyadenosine triphosphate (dATP) and fluorescent strand initiator 5'-Cy5-dA10 at different time points from Tjong et al. "Amplified on-chip fluorescence detection of DNA hybridization by surface-initiated enzymatic polymerization," *Anal. Chem.*, 2011; 83:5153-5159 (2011).

The methods of the invention may be used to modify terminal deoxynucleotidyl transferases (TdT), however other enzymes could be modified with similar methods. TdT is likely to be a successful starting enzyme because it is capable of 3'-extension activity using single strand initiating primers in a template-independent polymerization. However, prior to the invention described herein, there have been no reports of 3'-O-blocked nucleotides being incorporated into single-stranded oligonucleotide by an enzyme in the absence of a template. In fact, as Chang and Bollum reported, substitution of the 3'-hydroxyl group results in complete inactivity of available transferase enzymes. See Chang and Bollum, "Molecular Biology of Terminal Transferase, *CRC Critical Reviews in Biochemistry*, vol. 21 (1), p. 27-52 (1986), incorporated herein by reference in its entirety. Nonetheless, when TdT is used with natural dNTPs (i.e., not 3'-O-blocked), and without a template, oligonucleotide extension continues without stopping. Such uncontrolled incorporation is evidenced by the time-dependent gel electrophoresis images shown in FIG. 1. FIG. 1 shows an agarose gel of a solution phase polymerization reaction composed of terminal deoxynucleotidyl transferase (TdT), deoxyadenosine triphosphate (dATP) and fluorescent strand initiator 5'-Cy5-dA10 at different time points. (Adapted with permission from Tjong et al. "Amplified on-chip fluorescence detection of DNA hybridization by surface-initiated enzymatic polymerization," *Anal. Chem.*, 2011; 83:5153-5159 (2011), incorporated by reference herein in its entirety.) Additionally, TdT can extend primers in a near quantitative manner resulting in the addition of thousands of nucleotides, while TdT is likely to accept a wide variety of modified and substituted dNTPs as efficient substrates. Furthermore, a substantial library of mechanistic and structural information regarding TdT already exists. See Delarue et al., *EMBO J.* 2002; 21(3):427-39; Gouge et al., *J Mol Biol.* 2013 Nov. 15; 425(22):4334-52 and Romain et al., *Nucleic Acids Res.* 2009; 37(14):4642-56, both of which are incorporated by reference in their entireties.

It is known that TdT can use substrates having modifications and/or substitutions at the deoxyribose sugar ring as well as the purine/pyrimidine nucleobases. For example, TdT accepts bulky modifications at the C5 of pyrimidines and the C7 of purines. See Sorensen et al., "Enzymatic Ligation of Large Biomolecules to DNA," *ACS Nano* 2013, 7(9):8098-104; Figeys et al., *Anal. Chem.* 1994, 66(23): 4382-3; Li et al., *Cytometry*, 1995, 20(2):172-80, all of which are incorporated by reference in their entireties. In some instances, TdT can even accept non-nucleotide triphosphates. See Barone et al., *Nucleotides and Nucleic Acids* 2001, 20(4-7):1141-5, and Alexandrova et al., *Bioconjug Chem.*, 2007, 18(3):886-93, both of which are incorporated by reference in their entireties. However, there is little evidence in the prior art that TdT can accept 3'-O-blocked nucleotides. See, for example, Knapp et al., *Chem. Eur. J.*, 2011, 17:2903, incorporated herein by reference in its entirety. While the lack of activity of TdT was not a focus of Knapp et al., the authors reported that they tested their 3'-OH modified analog with TdT, and saw no incorporation of this relatively small 3'-OH modification into an oligonucleotide.

Native TdT is a very efficient enzyme. It has been demonstrated that TdT can polymerize extremely long homopolydeoxynucleotides of 1000 to 10,000 nucleotides in length (see Hoard et al., *J of Biol Chem*, 1969 244(19):5363-73; Bollum, *The Enzymes*, Volume 10, New York: Academic Press; 1974. p. 141-71; Tjong et al., *Anal Chem*, 2011, 83:5153-59, all of which are incorporated by reference in their entireties). Random sequence oligomers consisting of all four nucleotides have also been polymerized by TdT, however there are no reports of ordered polynucleotides being synthesized in the absence of a template. See Damiani, et al., *Nucleic Acids Res*, 1982, 10(20):6401-10, incorporated by reference herein in its entirety. Support-bound synthesis of polynucleotides by TdT is additionally supported by reports of homopolymer synthesis of 150 bps initiators covalently attached to self-assembled monolayers on gold surfaces. See Chow et al., *J Am Chem Soc* 2005;

127:14122-3, and Chow and Chilikoti, *Langmuir* 2007, 23:11712-7, both of which are incorporated by reference in their entireties. These authors also observed preference by TdT of dATP>dTTP>>dGTP≈dCTP for incorporation of homopolymers. In a more recent report, Tjong et al. demonstrated the TdT mediated synthesis of long (>1 Kb) homopolymer ssDNA from initiator primers immobilized on glass surfaces.

Figure 3:
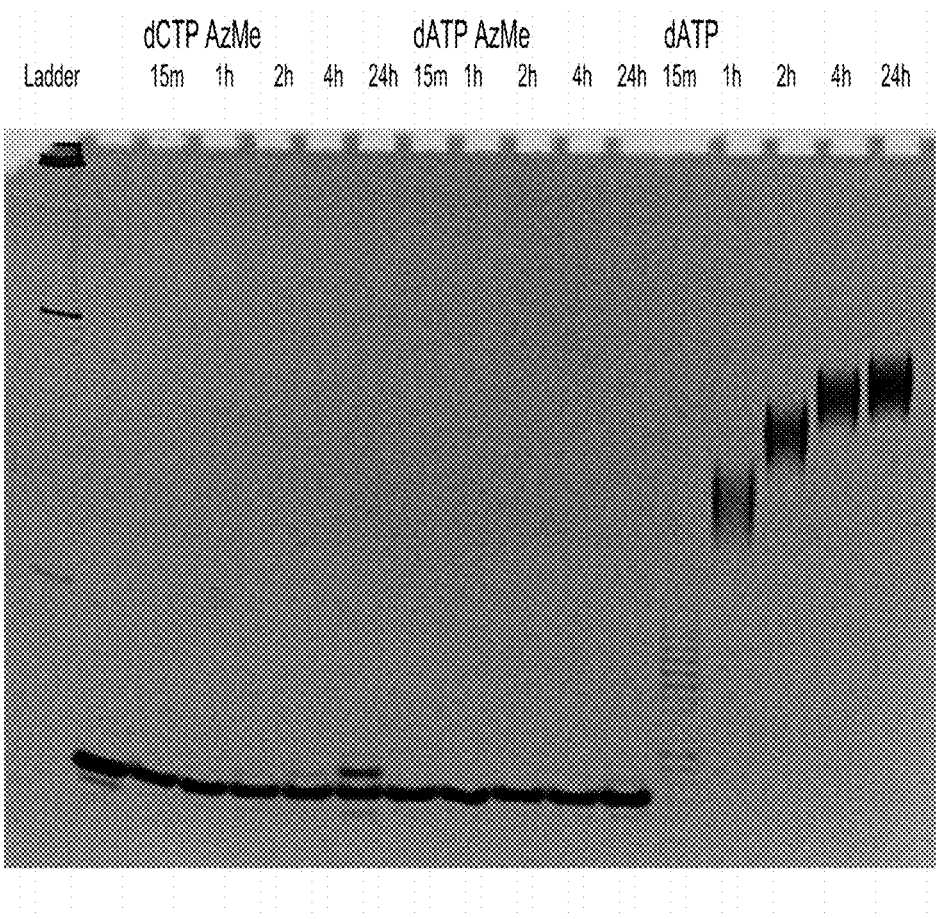
FIG. 3 shows the polyacrylamide gel analysis of a solution phase reaction time course of commercially-available TDT and a nucleic acid initiator with 3'-O-azidomethyl-dCTP or 3'-O-azidomethyl-dATP. Lane 1—100 bp ladder size standard, Lane 2—oligonucleotide standard, Lane 3—3'-O-azidomethyl-dCTP+TdT 15' reaction time, Lane 4—1 hour, Lane 5—2 hours, Lane 6—4 hours, Lane 7—24 hours, Lane 8—3'-O-azidomethyl-dATP+TdT 15' reaction time, Lane 9—1 hour, Lane 10—2 hours, Lane 10—4 hours, Lane 11—24 hours, Lane 12—dATP+TdT 15' reaction time, Lane 13—1 hour, Lane 14—4 hours, Lane 15—24 hours.

The distributive behavior of TdT is reinforced by FIG. 3, which shows a time course of a solution phase synthesis of 1-1.5 kb homopolymers. After each addition of an unmodified (natural) dNTP, the enzyme dissociates, thus allowing the random extension of any strand in the population. The distribution of product lengths in such a system should follow a Poisson distribution, as reported by Bollum and co-workers in 1974. If TdT were used with a terminating nucleotide species, i.e., one with the 3'-O-position blocked, the reaction should proceed to completion, resulting not in a distribution of product lengths, but essentially a pure product of a single nucleotide addition.

Nonetheless, as described above, nucleotide synthesis with 3'-O-blocked dNTPs does not proceed with commercially-available TdT proteins. This fact is reinforced by FIG. 3, which shows a gel shift assay used to monitor the solution phase incorporation kinetics of 3'-O-azidomethyl dATP and 3'-O-azidomethyl dCTP using a commercially-available, recombinant TdT. The data in FIG. 3 clearly show that neither 3'-O-modified dNTP analog is a substrate for TdT, i.e., there is no polynucleotide extension when compared to reactions containing dATP as a positive control (lanes 12 thru 15). FIG. 3, thus, adds further evidence that commercially-available TdTs are not able to synthesize oligomers by incorporating dNTPs with modified 3'-OHs.

With suitable modifications, a variety of different 3'-O-blocked dNTP analogs will be suitable for the controlled addition of nucleotides by TdT. Modified 3'-O-blocked dNTP analogs include, but are not limited to, the 3'-O-allyl, 3'-O-azidomethyl, 3'-O—NH$_2$, and 3'-OCH$_2$CN blocking groups. Overall, the choice of the 3'-O-blocking group will be dictated by: 1) the smallest possible bulk to maximize substrate utilization by TdT, which is likely to affect kinetic uptake, and 2) the blocking group with the mildest removal conditions, preferably aqueous, and in the shortest period of time. 3'-O-blocking groups that are the suitable for use with this invention are described in WO 2003/048387; WO 2004/018497; WO 1996/023807; WO 2008/037568; Hutter D, et al. *Nucleosides Nucleotides Nucleic Acids.* 2010, 29(11): 879-95; and Knapp et al., *Chem. Eur. J.,* 2011, 17:2903, all of which are incorporated by reference in their entireties.

Figure 4:
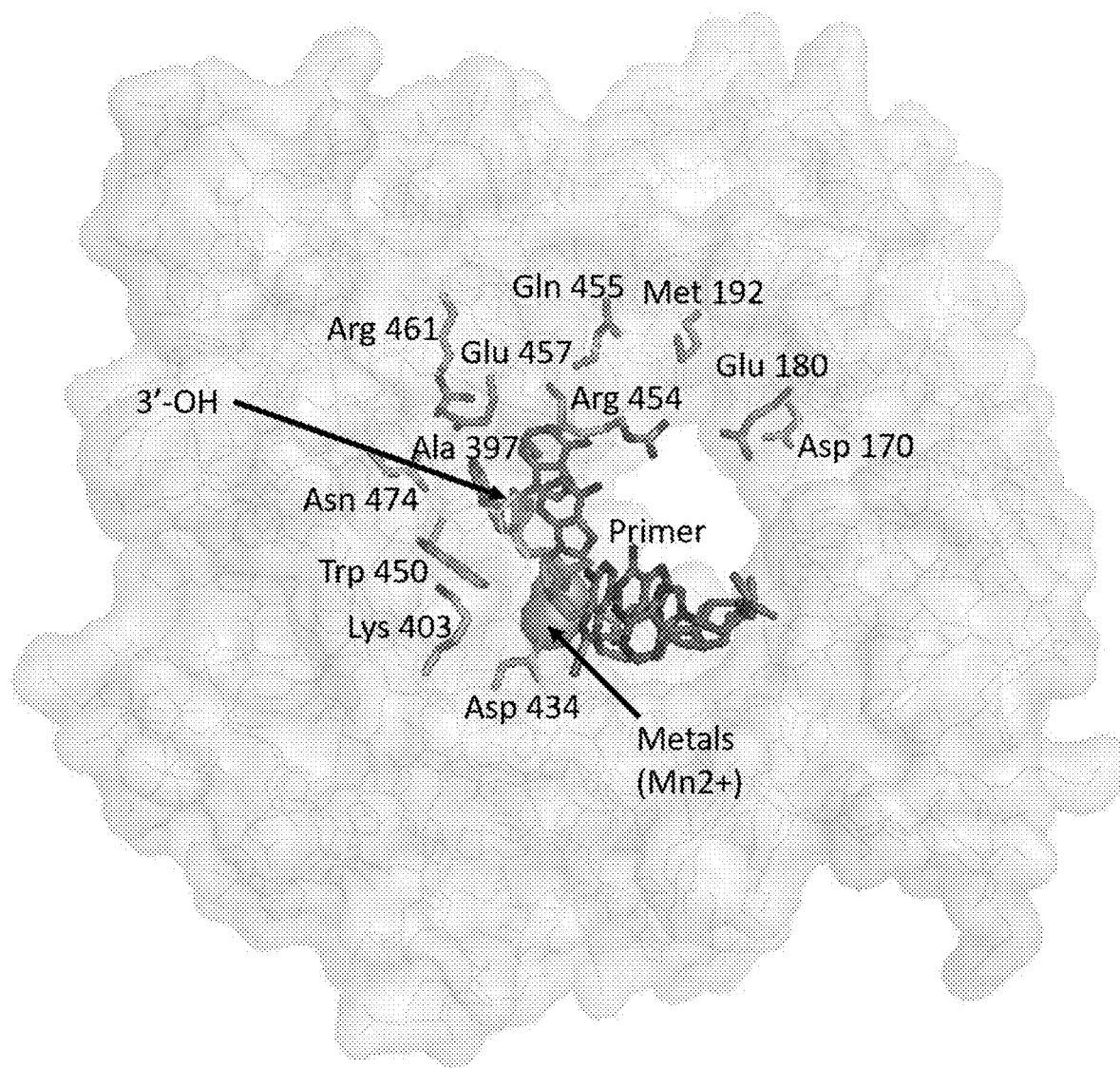
FIG. 4 shows a computer-generated image of the active site of TdT using the PDB crystal structure 4I29, showing the computationally docked catalytically productive position a 3'-O-dATP analog (blue, red, orange frame), each complexed to the two active-site metal ions (large greenspheres). Shown are the residues, that are in close proximity to the incoming dNTP and the targets of mutagenesis and screening.

A computational model of the active site of murine TdT was created to understand the structural basis for the lack of utilization of 3'-O-blocked dNTPs by TdT. Additionally, the computer model made it possible to "fit" various modified dNTPs into the active site. FIG. 4 shows the docking of a -dATP (shown in blue, red, magenta, orange) with murine TdT (see SEQ ID NO. 9, below) using the PDB crystal structure 4I29 and AutoDock 4.2 (Molecular Graphics Laboratory, Scripps Research Institute, La Jolla, Calif.).

The phosphate portions of the dATPs (orange) are in complex with the catalytic metal ions (green) while the alpha phosphate is positioned to be attacked by the 3'-OH of the bound oligonucleotide. The model shown in FIG. 4 indicates the choice of amino acid residues likely to interfere with the formation of a catalytically productive complex when a 3'-blocked dNTP is present. Other residues that may interact with the closest residues, like Glu 180 or Met 192, are also targets of modification. Amino acid numbering and positions are provided with reference to the murine TdT of SEQ ID NO. 9 but the referenced amino acid modifications are applicable to any TdT having similar sequence including the GGFRR or TGSR motifs.

AutoDock's predicted binding mode suggests that modification to the 3'-OH will change the electrostatic interactions between two residues, Arg336 and Arg454. Although Arg336 is near the reaction center in the active site, Arg 336 is highly conserved, and early studies found that replacement of Arg336 with Gly or Ala reduced dNTP activity by 10-fold (Yang B et al. J. Mol. Biol. 1994; 269(16):11859-68). Accordingly, one motif for modification is the GGFRR motif including Arg 336 in the above structural model.

Additionally, it is thought that Gly452 and Ser453 exist in a cis-peptide bond conformation (see Delarue et al., *EMBO J.* 2002; 21(3):427-39, incorporated herein by reference in its entirety) and that the guanidinium group of Arg336 assists in the stabilization of this conformation. The stability provided by Arg336 may help explain why substitutions at this position have a negative impact on the reactivity of modified TdT proteins. In some instances, the instability created by modifying position 336 may be overcome by using proline residues to stabilize cis-peptide bond conformation. However, if Arg336 is substituted, e.g., with alanine or glycine, the entire TGSR motif (positions 451, 452, 435, 454) may also have to be modified to compensate for this change. For example, the TGSR motif may be modified to TPSR or TGPR. Accordingly, the TGSR motif, including Gly452 in the above structural model was targeted for modification.

On the other hand, sequence analysis of the TdT family demonstrates a wide range of amino acids that can be accommodated at position 454. This analysis suggests structural flexibility at position 454, and surrounding residues. In another embodiment, substitutions at Arg454 to accommodate the steric bulk of a 3'-O-blocking group may require additional modifications to the α14 region to compensate for substitutions of glycine or alanine at Arg454. In other embodiments, substitutions to other residues in the all region may be required to compensate for substitution to Arg336 either instead of, or in addition to, modification of the TGSR motif.

While modification to Arg336 and Arg454 may change the binding interactions of 3'-O-modified dNTPs, it may also be necessary to explore substitutions that would result in improved steric interactions of 3'-O-modified dNTPs with TdT. In order to test computationally predicted enzyme variants that show increased substrate utilization of 3'-O-blocked dNTPs, synthetic genes specifying specific amino acid substitutions were generated in appropriate plasmid vectors and introduced into cells. After expression and isolation, protein variants were screened for activity by a polymerase incorporation assay with selected 3'-O-blocked dNTP analogs. FIG. 5 shows the results of the screening of various synthetically generated murine TdT variants. In some embodiments, single amino acid changes are important while in other, combinations of one & two amino acids also produce increased incorporation of 3'-O-blocked dNTPs. Interactions with residues such as Gly332, Gly333, Gly452, Thr451, Trp450, Ser453, and Q455 of murine TdT are important. Each of these residues is within 0.6 nm of the 3'-OH of a typical dNTP. These residues are also potential targets for substitution to allow the extra steric bulk of a 3'-blocking group like 3'-O-azidomethyl or 3'-O-aminoxy. Residues that are within 1.2 nm of the 3'-OH such as Glu457, Ala510, Asp509, Arg508, Lys199, Ser196, Met192, Glu180 or Leu161 may also potentially interfere with the substrate utilization of a 3'-O-blocked dNTP and are thus targets for substitution in addition to or in combination with Arg336 and Arg454. Additional residues of interest include Arg461 and Asn474.

While the TGSR and GGFRR motifs are highlighted here, modifications to the flanking amino acids such as Thr331, Gly337, Lys338, Gly341, or His342 are also contemplated for providing (alone or in combination) increased incorporation of 3'-O-blocked dNTPs as discussed herein. Various in silico modeled TdT modifications capable of increased incorporation are discussed in Example 2 below.

In addition to amino acid substitutions at positions 500-510 it may be necessary to delete residues to remove interference with a 3'-O-blocking group. Since these amino acids are located near the C-terminus of the protein, and exist in a relatively unstructured region, they may be deleted singly or altogether, either instead of or in combination with the modifications described above. In certain embodiments, insertion of residues into the modified TdT. For example, insertions of residues in the GGFRR or TGSR motifs or flanking regions can allow an increased rate of incorporation of 3'-O-blocked dNTP by the modified TdT. TdT modifications can include insertion of a Tyrosine residue between the Phe334 and Arg335 residues (or substitutions thereof) of the GGFRR motif.

Modified TdT's of the invention include those described in FIG. 5. Modified TdT's may include one or more of a modification to Glu180 including E 180L, E 180R, E 180D, or E 180K. Contemplated modifications to Met192 include, for example, M192E, M192W, M192K, or M192R. Contemplated modifications to Gln455 include, for example, Q455I. Contemplated modifications to Trp450 include, for example, W450H. Contemplated modifications to ARG454 include, for example, R4541, R454K, R454A, or R454T. Contemplated modifications to Arg461 include, for example, R461V and modifications to Asn474 may include N474R. In various embodiments combinations of two or more modified residues may be used such as, for example, E180D+W450H, E180K+R454A, M192K+E180K, E180K+R454I, E180D+M192E, E180D+M192E+R454T, or E180K+W450H.

As shown below, most TdTs include the GGFRR and TGSR motifs. In the following sequences, the GGFRR and TGSR motifs have been bolded and underlined for easy reference. Native calf thymus TdT is a candidate for alteration of the primary structure to achieve a suitable template-independent polymerase. However, a variety of other proteins may be explored to identify a candidate suitable for the use with 3'-O-blocked dNTP analogs, including human and murine TdT. The amino acid sequence corresponding to native calf TdT is listed in Table 1 as SEQ ID NO. 1, while the nucleic acid sequence is listed in Table 2 as SEQ ID NO. 2. In some embodiments, the resulting protein, adapted for sequence-specific de novo polynucleotide synthesis with 3'-O-modified dNTPs and NTPs, will be at least 85% identical, i.e., at least 90% identical, i.e., at least 93% identical, i.e., at least 95% identical, i.e., at least 97% identical, i.e., at least 98% identical, i.e., at least 99% identical, with SEQ ID NO. 1. Furthermore, it may be possible to truncate portions of the amino acid sequence of bovine TdT and still maintain catalytic activity.

TABLE 1

Amino Acid Sequence of Bovine TdT

SEQ ID NO. 1: (520 aa)
MAQQRQHQRL PMDPLCTASS GPRKKRPRQV GASMASPPHD

IKFQNLVLFI LEKKMGTTRR NFLMELARRK GFRVENELSD

SVTHIVAENN SGSEVLEWLQ VQNIRASSQL ELLDVSWLIE

SMGAGKPVEI TGKHQLVVRT DYSATPNPGF QKTPPLAVKK

ISQYACQRKT TLNNYNHIFT DAFEILAENS EFKENEVSYV

TFMRAASVLK SLPFTIISMK DTEGIPCLGD KVKCIIEEII

EDGESSEVKA VLNDERYQSF KLFTSVFGVG LKTSEKWFRM

GFRSLSKIMS DKTLKFTKMQ KAGFLYYEDL VSCVTRAEAE

AVGVLVKEAV WAFLPDAFVT MTGGFRRGKK IGHDVDFLIT

SPGSAEDEEQ LLPKVINLWE KKGLLLYYDL VESTFEKFKL

PSRQVDTLDH FQKCFLILKL HHQRVDSSKS NQQEGKTWKA

IRVDLVMCPY ENRAFALLGW TGSRQFERDI RRYATHERKM

MLDNHALYDK TKRVFLKAES EEEIFAHLGL DYIEPWERNA

TABLE 2

Nucleic Acid Sequence of Bovine TdT

SEQ ID NO. 2: (1923 nt)
ctcttctgga gataccactt gatggcacag cagaggcagc atcagcgtct tcccatggat ccgctgtgca cagcctcctc aggccctcgg aagaagagac ccaggcaggt gggtgcctca atggcctccc ctcctcatga catcaagttt caaaatttgg tcctcttcat tttggagaag aaaatgggaa ccacccgcag aaacttcctc atggagctgg ctcgaaggaa aggtttcagg gttgaaaatg agctcagtga ttctgtcacc cacattgtag cagaaaacaa ctctggttca gaggttctcg agtggcttca ggtacagaac ataagagcca gctcgcagct agaactcctt gatgtctcct ggctgatcga aagtatggga gcaggaaaac cagtggagat tacaggaaaa caccagcttg ttgtgagaac agactattca gctacccccaa acccaggctt ccagaagact ccaccacttg ctgtaaaaaa gatctcccag tacgcgtgtc aaagaaaaac cactttgaac aactataacc acatattcac ggatgccttt gagatactgg ctgaaaattc tgagtttaaa gaaaatgaag tctcttatgt gacatttatg agagcagctt ctgtacttaa atctctgcca ttcacaatca tcagtatgaa ggatacagaa ggaattccct gcctggggga caaggtgaag tgtatcatag aggaaattat tgaagatgga gaaagttctg aagttaaagc tgtgttaaat gatgaacgat atcagtcctt caaactcttt acttctgttt ttggagtggg actgaagaca tctgagaaat ggttcaggat ggggttcaga tctctgagta

TABLE 2-continued

Nucleic Acid Sequence of Bovine TdT

```
aaataatgtc agacaaaacc ctgaaattca caaaaatgca
gaaagcagga tttctctatt atgaagacct tgtcagctgc
gtgaccaggg ccgaagcaga ggcggttggc gtgctggtta
aagaggctgt gtgggcattt ctgccggatg cctttgtcac
catgacagga ggattccgca ggggtaagaa gattgggcat
gatgtagatt ttttaattac cagcccagga tcagcagagg
atgaagagca acttttgcct aaagtgataa acttatggga
aaaaaaggga ttacttttat attatgacct tgtggagtca
acatttgaaa agttcaagtt gccaagcagg caggtggata
ctttagatca ttttcaaaaa tgctttctga ttttaaaatt
gcaccatcag agagtagaca gtagcaagtc caaccagcag
gaaggaaaga cctggaaggc catccgtgtg gacctggtta
tgtgcccta cgagaaccgt gcctttgccc tgctaggctg
gactggctcc cggcagtttg agagagacat ccggcgctat
gccacacacg agcggaagat gatgctggat aaccacgctt
tatatgacaa gaccaagagg gtatttctca aagcggaaag
tgaagaagaa atctttgcac atctgggatt ggactacatt
gaaccatggg aaagaaatgc ttaggagaaa gctgtcaact
tttttctttt ctgttctttt tttcaggtta gacaaattat
gcttcatatt ataatgaaag atgccttagt caagtttggg
attctttaca ttttaccaag atgtagattg cttctagaaa
taagtagttt tggaaacgtg atcaggcacc ccctgggtta
tgctctggca agccatttgc aggactgatg tgtagaactc
gcaatgcatt ttccataaa acagtgttgg aattggtggc
tcatttccag ggaagttcat caaagcccac tttgcccaca
gtgtagctga aatactgtat acttgccaat aaaaatagga
aac
```

Additionally, to make isolation of recombinant proteins easier, it is common to append an N-terminal His tag sequence to the recombinant protein (see Boule J-B et al., *Molecular Biotechnology*, 1998; 10:199-208, incorporated by reference herein in its entirety), which is used in combination with an affinity column (Hitrap, Amersham Pharmacia Biotech, Uppsala, Sweden). Alternatively, N-terminal truncated forms of the enzyme with appended His-tag sequence will work with the current invention (see, e.g., U.S. Pat. No. 7,494,797, incorporated by reference herein in its entirety). His-tagged Bovine TdT amino acid sequences are shown below in Tables 3, 5, and 7, while His-tagged Bovine TdT nucleic acid sequences are shown below in Tables 4, 6, and 8. His tags may be engineered at other positions as required. In some embodiments, the resulting protein, adapted for sequence-specific de novo polynucleotide synthesis with 3'-O-modified dNTPs and NTPs, will be at least 85% identical, i.e., at least 90% identical, i.e., at least 93% identical, i.e., at least 95% identical, i.e., at least 97% identical, i.e., at least 98% identical, i.e., at least 99% identical, with SEQ ID NOS. 3, 5, or 7.

TABLE 3

Amino Acid Sequence of a Δ138 and His-tagged Bovine TdT.

SEQ ID No. 3: (392 aa)
Met Arg Gly Ser His His His His His His Arg Thr

Asp Tyr Ser Ala Thr Pro Asn Pro Gly Phe Gln Lys

Thr Pro Pro Leu Ala Val Lys Lys Ile Ser Gln Tyr

Ala Cys Gln Arg Lys Thr Thr Leu Asn Asn Tyr Asn

His Ile Asp Ala Phe Glu Ile Leu Ala Glu Asn Ser

Glu Phe Lys Glu Asn Glu Val Ser Tyr Val Thr Phe

Met Arg Ala Ala Ser Val Leu Lys Ser Leu Pro Phe

Thr Ile Ile Ser Met Lys Asp Thr Phe Thr Glu Gly

Ile Pro Cys Leu Gly Asp Lys Val Lys Cys Ile Ile

Glu Glu Ile Ile Glu Asp Gly Glu Ser Ser Glu Val

Lys Ala Val Leu Asn Asp Glu Arg Tyr Gln Ser Phe

Lys Leu Ser Val Phe Gly Val Gly Leu Lys Thr Ser

Glu Lys Trp Phe Arg Met Gly Phe Thr Phe Arg Ser

Leu Ser Lys Ile Met Ser Asp Lys Thr Leu Lys Lys

Met Gln Lys Ala Gly Phe Leu Tyr Tyr Glu Asp Leu

Val Ser Cys Val Thr Arg Ala Glu Ala Glu Ala Val

Gly Val Leu Val Lys Glu Ala Val Trp Ala Phe Leu

Pro Asp Ala Phe Val Thr Met Thr Gly Gly Phe Arg

Arg Gly Lys Lys Ile Gly His Asp Val Asp Phe Leu

Ile Thr Ser Pro Gly Ser Ala Glu Asp Glu Glu Gln

Leu Leu Pro Lys Val Ile Asn Leu Trp Glu Lys Lys

Gly Leu Leu Leu Tyr Tyr Asp Leu Val Glu Ser Thr

Phe Glu Lys Phe Lys Phe Thr Leu Pro Ser Arg Gln

Val Asp Thr Leu Asp His Phe Gln Lys Cys Phe Leu

Ile Leu Lys Leu His His Gln Arg Val Asp Ser Ser

Lys Ser Asn Gln Gln Glu Gly Lys Thr Trp Lys Ala

Ile Arg Val Asp Leu Val Met Cys Pro Tyr Glu Asn

Arg Ala Phe Ala Leu Leu Gly Trp Thr Gly Ser Arg

Gln Phe Glu Arg Asp Ile Arg Arg Tyr Ala Thr His

Glu Arg Lys Met Met Leu Asp Asn His Ala Leu Tyr

Asp Lys Thr Lys Arg Val Phe Leu Lys Ala Glu Ser

Glu Glu Glu Ile Phe Ala His Leu Gly Leu Asp Tyr

Ile Glu Pro Trp Glu Arg Asn Ala

TABLE 4

Nucleotide Sequence of a Δ138 and His-tagged Bovine TdT.

SEQ ID No. 4: (1187 nt)
```
atgagaggat cgcatcacca tcaccatcac agaacagact
attcagctac cccaaaccca ggcttccaga agactccacc
acttgctgta aaaagatct cccagtacgc gtgtcaaaga
aaaaccactt tgaacaacta taaccacata ttcacggatg
cctttgagat actggctgaa aattctgagt ttaaagaaaa
tgaagtctct tatgtgacat ttatgagagc agcttctgta
cttaaatctc tgccattcac aatcatcagt atgaaggata
cagaaggaat tccctgcctg ggggacaagg tgaagtgtat
catagaggaa attattgaag atggagaaag ttctgaagtt
aaagctgtgt taaatgatga acgatatcag tccttcaaac
tctttacttc tgttttttgga gtgggactga agacatctga
gaaatggttc aggatggggt tcagatctct gagtaaaata
atgtcagaca aaaccctgaa attcacaaaa atgcagaaag
caggatttct ctattatgaa gaccttgtca gctgcgtgac
cagggccgaa gcagaggcgg ttggcgtgct ggttaaagag
gctgtgtggg catttctgcc ggatgccttt gtcaccatga
caggaggatt ccgcagggt aagaagattg gcatgatgt
agatttttta attaccagcc caggatcagc agaggatgaa
gagcaacttt tgcctaaagt gataaactta tgggaaaaaa
agggattact tttatattat gaccttgtgg agtcaacatt
tgaaaagttc aagttgccaa gcaggcaggg ggatacttta
gatcatttc aaaaatgctt tctgattta aaattgcacc
atcagagagt agacagtagc aagtccaacc agcaggaagg
aaagacctgg aaggccatcc gtgtggacct ggttatgtgc
ccctacgaga accgtgcctt tgccctgcta ggctggactg
gctcccggca gtttgagaga gacatccggc gctatgccac
acacgagcgg aagatgatgc tggataacca cgctttatat
gacaagacca agagggtatt tctcaaagcg gaaagtgaag
aagaaatctt tgcacatctg ggattggact acattgaacc
atgggaaaga aatgcttaag cttgcgc
```

TABLE 5

Amino Acid Sequence of a Δ151 and His-tagged Bovine TdT.

SEQ ID No. 5: (379 aa)
Met Arg Gly Ser His His His His His His Lys Thr
Pro Pro Leu Ala Val Lys Lys Ile Ser Gln Tyr Ala
Cys Gln Arg Lys Thr Thr Leu Asn Asn Tyr Asn His
Ile Asp Ala Phe Glu Ile Leu Ala Glu Asn Ser Glu

TABLE 5-continued

Amino Acid Sequence of a Δ151 and His-tagged Bovine TdT.

Phe Lys Glu Asn Glu Val Ser Tyr Val Thr Phe Met
Arg Ala Ala Ser Val Leu Lys Ser Leu Pro Phe Thr
Ile Ile Ser Met Lys Asp Thr Phe Thr Glu Gly Ile
Pro Cys Leu Gly Asp Lys Val Lys Cys Ile Ile Glu
Glu Ile Ile Glu Asp Gly Glu Ser Ser Glu Val Lys
Ala Val Leu Asn Asp Glu Arg Tyr Gln Ser Phe Lys
Leu Ser Val Phe Gly Val Gly Leu Lys Thr Ser Glu
Lys Trp Phe Arg Met Gly Phe Thr Phe Arg Ser Leu
Ser Lys Ile Met Ser Asp Lys Thr Leu Lys Lys Met
Gln Lys Ala Gly Phe Leu Tyr Tyr Glu Asp Leu Val
Ser Cys Val Thr Arg Ala Glu Ala Glu Ala Val Gly
Val Leu Val Lys Glu Ala Val Trp Ala Phe Leu Pro
Asp Ala Phe Val Thr Met Thr Gly Gly Phe Arg Arg
Gly Lys Lys Ile Gly His Asp Val Asp Phe Leu Ile
Thr Ser Pro Gly Ser Ala Glu Asp Glu Glu Gln Leu
Leu Pro Lys Val Ile Asn Leu Trp Glu Lys Lys Gly
Leu Leu Leu Tyr Tyr Asp Leu Val Glu Ser Thr Phe
Glu Lys Phe Lys Phe Thr Leu Pro Ser Arg Gln Val
Asp Thr Leu Asp His Phe Gln Lys Cys Phe Leu Ile
Leu Lys Leu His His Gln Arg Val Asp Ser Ser Lys
Ser Asn Gln Gln Glu Gly Lys Thr Trp Lys Ala Ile
Arg Val Asp Leu Val Met Cys Pro Tyr Glu Asn Arg
Ala Phe Ala Leu Leu Gly Trp Thr Gly Ser Arg Gln
Phe Glu Arg Asp Ile Arg Arg Tyr Ala Thr His Glu
Arg Lys Met Met Leu Asp Asn His Ala Leu Tyr Asp
Lys Thr Lys Arg Val Phe Leu Lys Ala Glu Ser Glu
Glu Glu Ile Phe Ala His Leu Gly Leu Asp Tyr Ile
Glu Pro Trp Glu Arg Asn Ala

TABLE 6

Nucleotide Sequence of a Δ151 and His-tagged Bovine TdT.

SEQ ID No. 6: (1148 nt)
```
atgagaggat cgcatcacca tcaccatcac aagactccac
cacttgctgt aaaaagatc tcccagtacg cgtgtcaaag
aaaaccact tgaacaact ataaccacat attcacggat
gcctttgaga tactggctga aaattctgag tttaaagaaa
atgaagtctc ttatgtgaca tttatgagag cagcttctgt
acttaaatct ctgccattca caatcatcag tatgaaggat
```

TABLE 6-continued

Nucleotide Sequence of a Δ151 and His-tagged Bovine TdT.

```
acagaaggaa ttccctgcct gggggacaag gtgaagtgta
tcatagagga aattattgaa gatggagaaa gttctgaagt
taaagctgtg ttaaatgatg aacgatatca gtccttcaaa
ctctttactt ctgttttttgg agtgggactg aagacatctg
agaaatggtt caggatgggg ttcagatctc tgagtaaaat
aatgtcagac aaaaccctga aattcacaaa aatgcagaaa
gcaggatttc tctattatga agaccttgtc agctgcgtga
ccagggccga agcagaggcg gttggcgtgc tggttaaaga
ggctgtgtgg gcatttctgc cggatgcctt tgtcaccatg
acaggaggat ccgcagggg taagaagatt gggcatgatg
tagattttt aattaccagc ccaggatcag cagaggatga
agagcaactt tgcctaaag tgataaactt atgggaaaaa
aagggattac ttttatatta tgaccttgtg gagtcaacat
ttgaaaagtt caagttgcca agcaggcagg tggatacttt
agatcatttt caaaaatgct ttctgatttt aaaattgcac
catcagagag tagacagtag caagtccaac cagcaggaag
gaaagacctg gaaggccatc cgtgtggacc tggttatgtg
cccctacgag aaccgtgcct tgccctgct aggctggact
ggctcccggc agtttgagag agacatccgg cgctatgcca
cacacgagcg gaagatgatg ctggataacc acgctttata
tgacaagacc aagagggtat ttctcaaagc ggaaagtgaa
gaagaaatct ttgcacatct gggattggac tacattgaac
catgggaaag aaatgcttaa gcttgcgc
```

TABLE 7

Amino Acid Sequence of a Δ160 and His-tagged Bovine TdT.

SEQ ID No. 7: (370 aa)
```
Met Arg Gly Ser His His His His His His Ile Ser
Gln Tyr Ala Cys Gln Arg Lys Thr Thr Leu Asn Asn
Tyr Asn His Ile Asp Ala Phe Glu Ile Leu Ala Glu
Asn Ser Glu Phe Lys Glu Asn Glu Val Ser Tyr Val
Thr Phe Met Arg Ala Ala Ser Val Leu Lys Ser Leu
Pro Phe Thr Ile Ile Ser Met Lys Asp Thr Phe Thr
Glu Gly Ile Pro Cys Leu Gly Asp Lys Val Lys Cys
Ile Ile Glu Glu Ile Ile Glu Asp Gly Glu Ser Ser
Glu Val Lys Ala Val Leu Asn Asp Glu Arg Tyr Gln
Ser Phe Lys Leu Ser Val Phe Gly Val Gly Leu Lys
Thr Ser Glu Lys Trp Phe Arg Met Gly Phe Thr Phe
```

TABLE 7-continued

Amino Acid Sequence of a Δ160 and His-tagged Bovine TdT.

```
Arg Ser Leu Ser Lys Ile Met Ser Asp Lys Thr Leu
Lys Lys Met Gln Lys Ala Gly Phe Leu Tyr Tyr Glu
Asp Leu Val Ser Cys Val Thr Arg Ala Glu Ala Glu
Ala Val Gly Val Leu Val Lys Glu Ala Val Trp Ala
Phe Leu Pro Asp Ala Phe Val Thr Met Thr Gly Gly
Phe Arg Arg Gly Lys Lys Ile Gly His Asp Val Asp
Phe Leu Ile Thr Ser Pro Gly Ser Ala Glu Asp Glu
Glu Gln Leu Leu Pro Lys Val Ile Asn Leu Trp Glu
Lys Lys Gly Leu Leu Leu Tyr Tyr Asp Leu Val Glu
Ser Thr Phe Glu Lys Phe Lys Phe Thr Leu Pro Ser
Arg Gln Val Asp Thr Leu Asp His Phe Gln Lys Cys
Phe Leu Ile Leu Lys Leu His His Gln Arg Val Asp
Ser Ser Lys Ser Asn Gln Gln Glu Gly Lys Thr Trp
Lys Ala Ile Arg Val Asp Leu Val Met Cys Pro Tyr
Glu Asn Arg Ala Phe Ala Leu Leu Gly Trp Thr Gly
Ser Arg Gln Phe Glu Arg Asp Ile Arg Arg Tyr Ala
Thr His Glu Arg Lys Met Met Leu Asp Asn His Ala
Leu Tyr Asp Lys Thr Lys Arg Val Phe Leu Lys Ala
Glu Ser Glu Glu Glu Ile Phe Ala His Leu Gly Leu
Asp Tyr Ile Glu Pro Trp Glu Arg Asn Ala
```

TABLE 8

Nucleotide Sequence of a Δ160 and His-tagged Bovine TdT.

SEQ ID No. 8: (1121 nt)
```
atgagaggat cgcatcacca tcaccatcac atctcccagt
acgcgtgtca agaaaaaacc actttgaaca actataacca
catattcacg gatgcctttg agatactggc tgaaaattct
gagtttaaag aaaatgaagt ctcttatgtg acatttatga
gagcagcttc tgtacttaaa tctctgccat tcacaatcat
cagtatgaag gatacagaag gaattccctg cctgggggac
aaggtgaagt gtatcataga ggaaattatt gaagatggag
aaagttctga agttaaagct gtgttaaatg atgaacgata
tcagtccttc aaactcttta cttctgtttt tggagtggga
ctgaagacat ctgagaaatg gttcaggatg gggttcagat
ctctgagtaa aataatgtca gacaaaaccc tgaaattcac
aaaaatgcag aaagcaggat ttctctatta tgaagacctt
gtcagctgcg tgaccagggc cgaagcagag gcggttggcg
tgctggttaa agaggctgtg tgggcatttc tgccggatgc
```

TABLE 8-continued

Nucleotide Sequence of a Δ160 and
His-tagged Bovine TdT.

ctttgtcacc atgacaggag gattccgcag gggtaagaag attgggcatg atgtagattt tttaattacc agcccaggat cagcagagga tgaagagcaa cttttgccta aagtgataaa cttatgggaa aaaaagggat tacttttata ttatgaccttt gtggagtcaa catttgaaaa gttcaagttg ccaagcaggc aggtggatac tttagatcat tttcaaaaat gctttctgat tttaaaattg caccatcaga gagtagacag tagcaagtcc aaccagcagg aaggaaagac ctggaaggcc atccgtgtgg acctggttat gtgccctac gagaaccgtg cctttgccct gctaggctgg actggctccc ggcagtttga gagagacatc cggcgctatg ccacacacga gcggaagatg atgctggata accacgcttt atatgacaag accaagaggg tatttctcaa agcggaaagt gaagaagaaa tctttgcaca tctgggattg gactacattg aaccatggga aagaaatgct taagcttgcg c

TABLE 9

Amino Acid Sequence of murine TdT

SEQ ID NO. 9: (510 aa)
MDPLQAVHLG PRKKRPRQLG TPVASTPYDI RFRDLVLFIL

EKKMGTTRRA FLMELARRKG FRVENELSDS VTHIVAENNS

GSDVLEWLQL QNIKASSELE LLDISWLIEC MGAGKPVEMM

GRHQLVVNRN SSPSPVPGSQ NVPAPAVKKI SQYACQRRTT

LNNYNQLFTD ALDILAENDE LRENEGSCLA FMRASSVLKS

LPFPITSMKD TEGIPCLGDK VKSIIEGIIE DGESSEAKAV

LNDERYKSFK LFTSVFGVGL KTAEKWFRMG FRTLSKIQSD

KSLRFTQMQK AGFLYYEDLV SCVNRPEAEA VSMLVKEAVV

TFLPDALVTM TGGFRRGKMT GHDVDFLITS PEATEDEEQQ

LLHKVTDFWK QQGLLLYCDI LESTFEKFKQ PSRKVDALDH

FQKCFLILKL DHGRVHSEKS GQQEGKGWKA IRVDLVMCPY

DRRAFALLGW TGSRQFERDL RRYATHERKM MLDNHALYDR

TKRVFLEAES EEEIFAHLGL DYIEPWERNA

A variety of 3'-O-modified dNTPs and NTPs may be used with the disclosed proteins for de novo synthesis. In some embodiments, the preferred removable 3'-O-blocking group is a 3'-O-amino, a 3'-O-allyl or a 3'-O-azidomethyl. In other embodiments, the removable 3'-O-blocking moiety is selected from the group consisting of O-phenoxyacetyl; O-methoxyacetyl; 0-acetyl; O-(p-toluene)-sulfonate; O-phosphate; O-nitrate; O-[4-methoxy]-tetrahydrothiopyranyl; O-tetrahydrothiopyranyl; O-[5-methyl]-tetrahydrofuranyl; O-[2-methyl,4-methoxy]-tetrahydropyranyl; O-[5-methyl]-tetrahydropyranyl; and O-tetrahydrothiofuranyl (see U.S. Pat. No. 8,133,669). In other embodiments the removable blocking moiety is selected from the group consisting of esters, ethers, carbonitriles, phosphates, carbonates, carbamates, hydroxylamine, borates, nitrates, sugars, phosphoramide, phosphoramidates, phenylsulfenates, sulfates, sulfones and amino acids (see Metzker M L et al. Nuc Acids Res. 1994; 22(20):4259-67, U.S. Pat. Nos. 5,763, 594, 6,232,465, 7,414,116; and 7,279,563, all of which are incorporated by reference in their entireties).

Synthesis of Exemplary 3'-O-Blocked dNTP Analogs

FIG. 6 shows four exemplary 3'-O-blocked dNTP analogs, namely 3'-O-azidomethyl-dATP, 3'-O-azidomethyl-dCTP, 3'-O-azidomethyl-dGTP, and 3'-O-azidomethyl-dTTP. The synthesis of each 3'-O-azidomethyl analog is described below and detailed in FIGS. 7-12. The 3'-O-blocked dNTP analogs can also be purchased from specialty suppliers, such as Azco Biotech, Oceanside, Calif. It is to be understood that corresponding 3'-O-blocked ribonucleotides can be formed with similar synthetic methods to enable the creation of custom RNA oligos.

Figure 7:
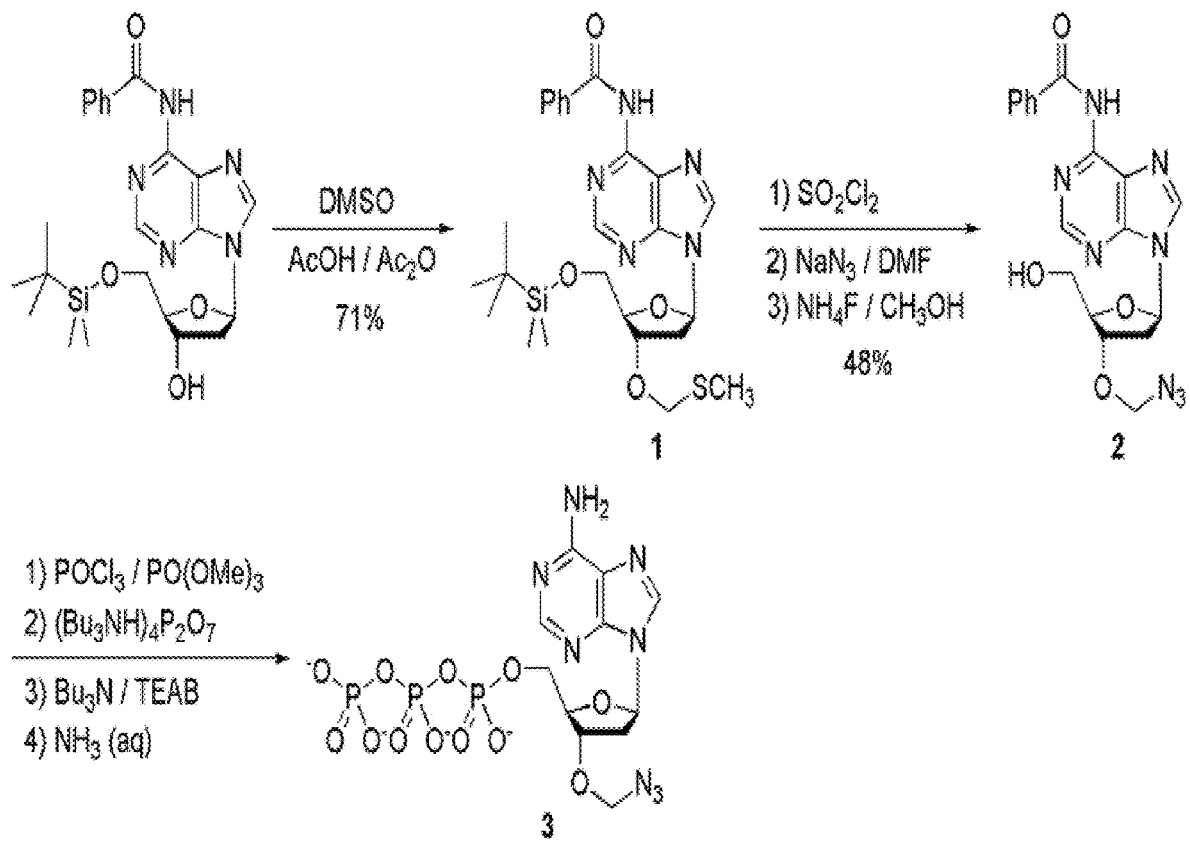
FIG. 7 shows a synthetic scheme for producing 3'-O-azidomethyl deoxyadenosine triphosphate (3'-O-azidomethyl-dATP).
Figure 8:
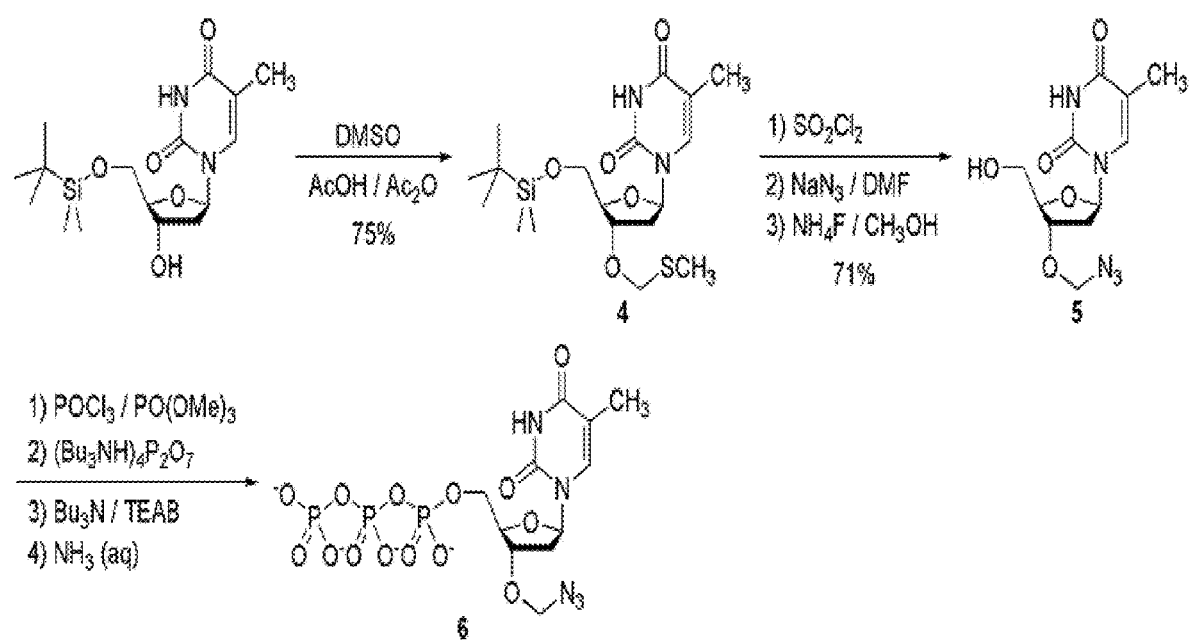
FIG. 8 shows a synthetic scheme for producing 3'-O-azidomethyl deoxythymidine triphosphate (3'-O-azidomethyl-dTTP).
Figure 9:
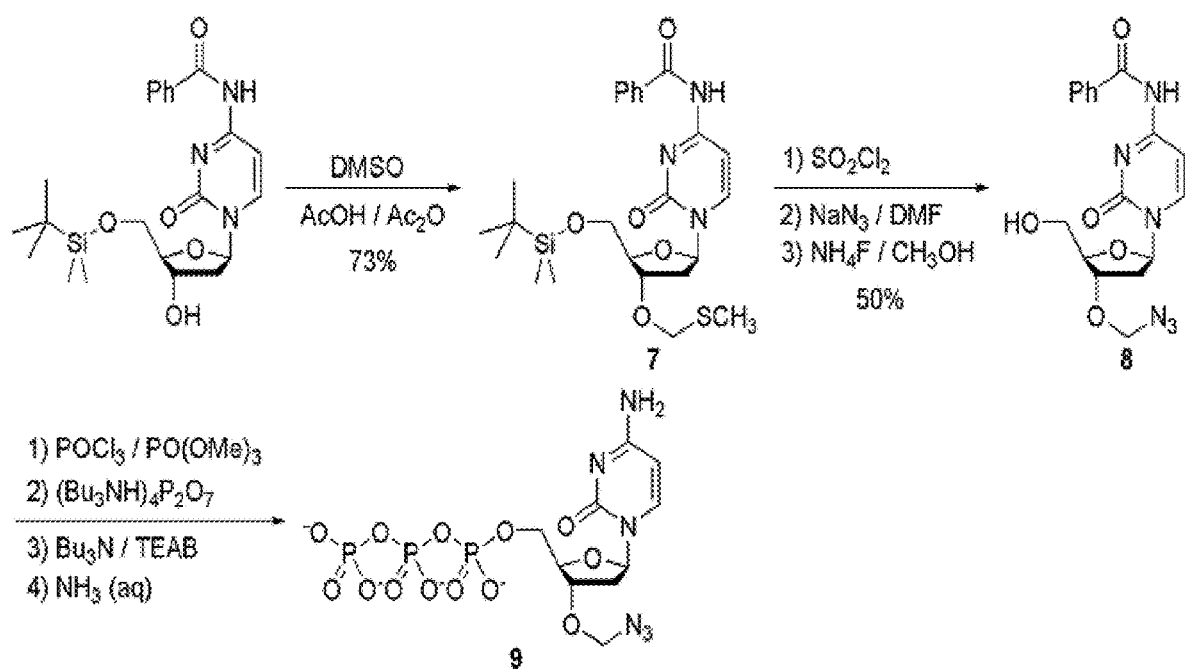
FIG. 9 shows a synthetic scheme for producing 3'-O-azidomethyl deoxycytidine triphosphate (3'-O-azidomethyl-dCTP).
Figure 10:
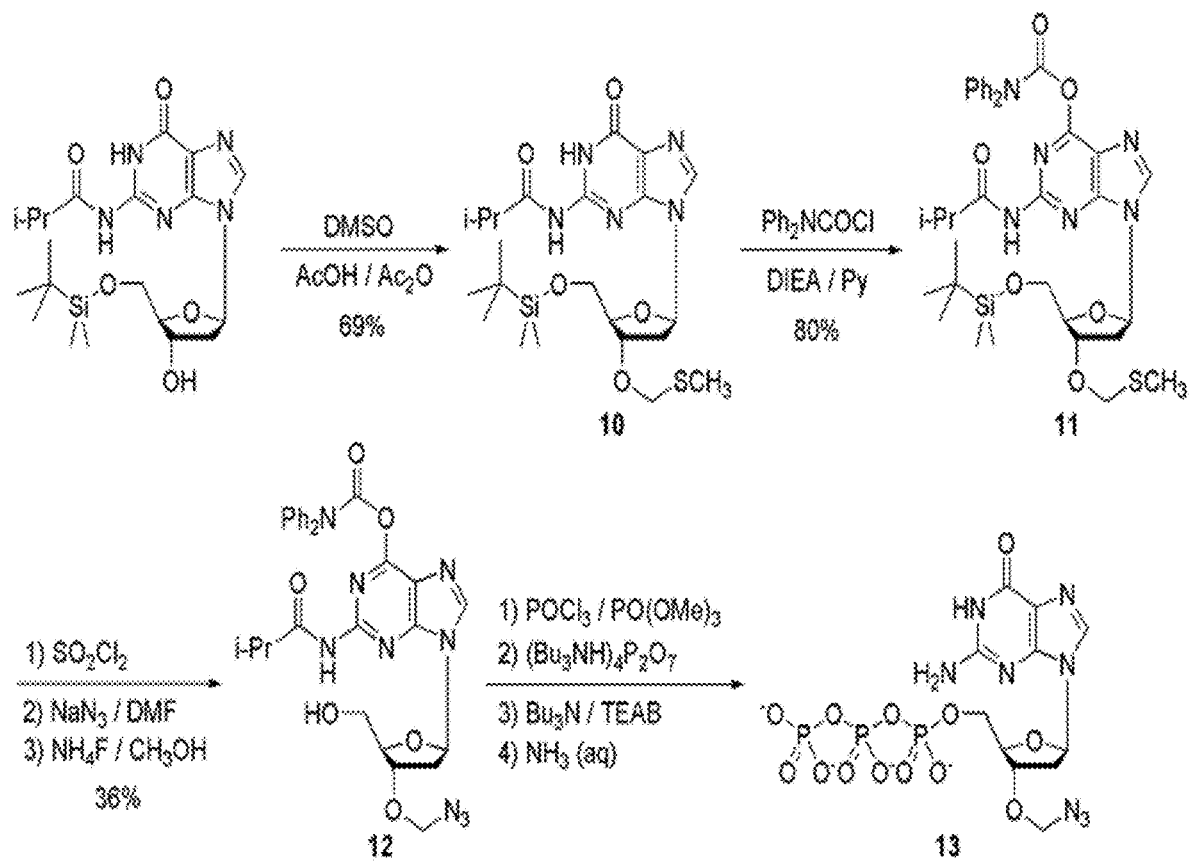
FIG. 10 shows a synthetic scheme for producing 3'-O-azidomethyl deoxyguanosine triphosphate (3'-O-azidomethyl-dGTP).
Figure 11:
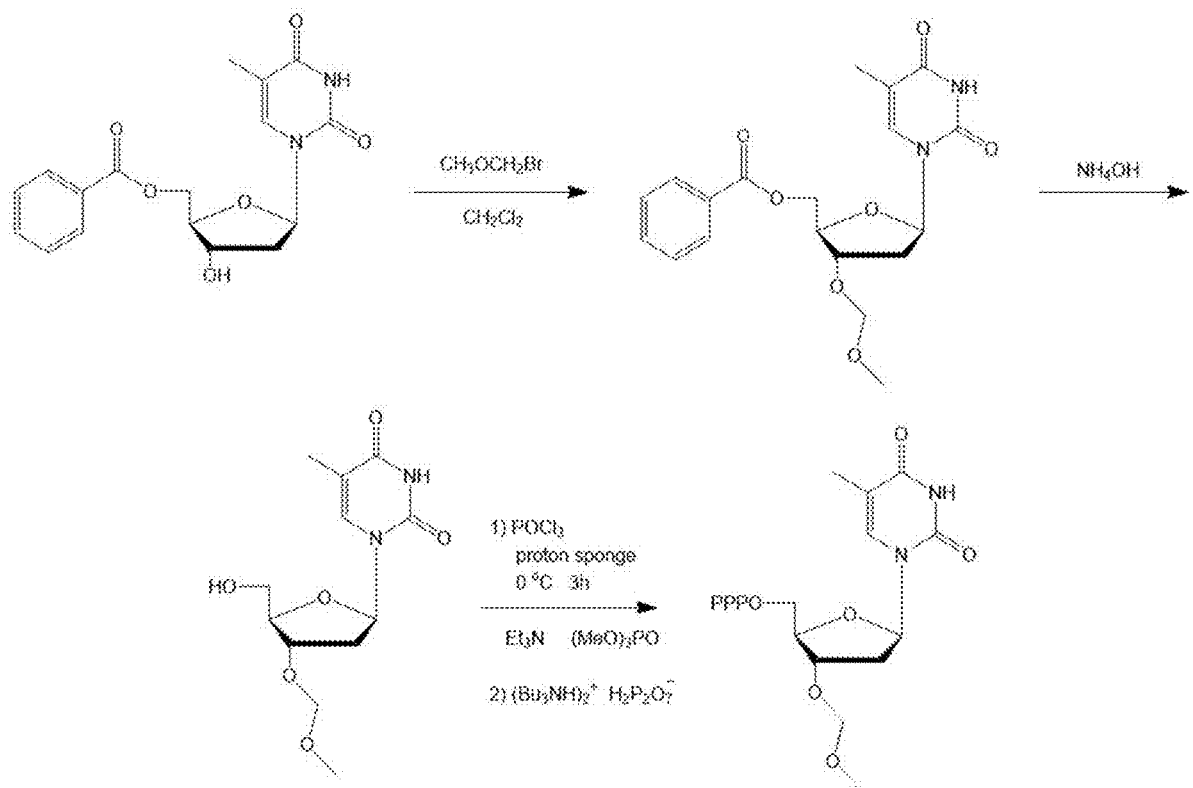
FIG. 11 shows a synthetic scheme for producing 3'-O-methoxymethyl deoxythymidine triphosphate (3'-O-MOM-dTTP).
Figure 12:
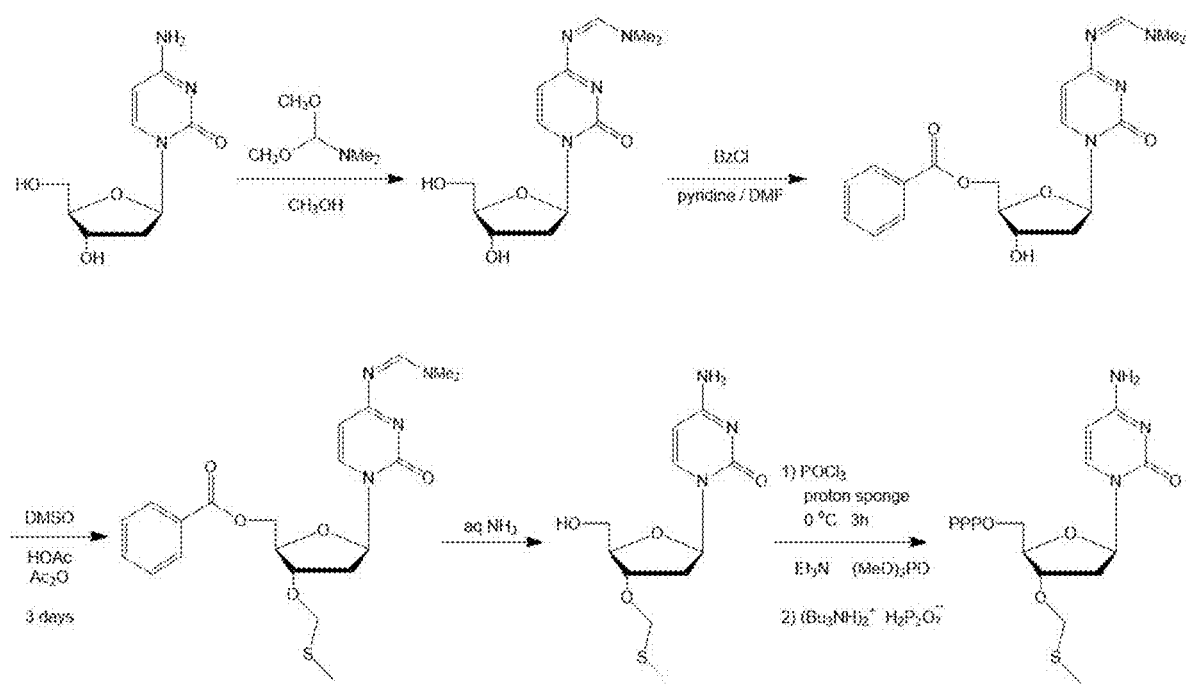
FIG. 12 shows a synthetic scheme for producing 3'-O-thiomethyl deoxycytidine triphosphate (3'-O-MTM-dCTP).

3'-O-azidomethyl-dATP:

With reference to FIG. 7, a solution of $N^6$-benzoyl-5'-O-(tert-butyldimethylsilyl)-2'-deoxyadenosine (3.0 g; 6.38 mmol) [CNH Technologies, Woburn, Mass.] in DMSO (12 ml), acetic acid (5.5 ml) and acetic anhydride (17.6 ml) was prepared. The mixture was stirred at room temperature for 48 h. Approximately 100 ml of a saturated $NaHCO_3$ solution was added and the aqueous layer was extracted with $CH_2Cl_2$. The combined organic extract was washed with saturated $NaHCO_3$ solution and dried over $Na_2SO_4$. The residue was purified by flash column chromatography (hexane/ethyl acetate, 1:1 to 1:4) to recover $N^6$-Benzoyl-3'-O-(methylthiomethyl)-5'-O-(tert-butyldimethylsilyl)-2'-deoxyadenosine (shown as compound 1 in FIG. 7) as a white powder (2.4 g; 71% yield). 400 mg of $N^6$-Benzoyl-3'-O-(methylthiomethyl)-5'-O-(tert-butyldimethylsilyl)-2'-deoxyadenosine was dissolved in dry $CH_2Cl_2$ (7 ml) under nitrogen to create a solution (0.76 mmol). Cyclohexene (400 μl), and $SO_2Cl_2$(155 μl; 1.91 mmol, redistilled) were then added. The reaction mixture was stirred at 0° C. for 2 h. The solvent was then removed under reduced pressure and then under a high-vacuum pump for 10 min. The resulting residue was dissolved in dry DMF (5 ml) and reacted with $NaN_3$ (400 mg; 6.6 mmol) at room temperature for 3 h. The reaction mixture was dispersed in distilled water (50 ml) and extracted with $CH_2Cl_2$. The combined organic layer was dried over $Na_2SO_4$ and concentrated under reduced pressure. The residue was dissolved in MeOH (5 ml) and stirred with $NH_4F$ (300 mg; 8.1 mmol) at room temperature for 24 h. The solvent was then removed under reduced pressure. The reaction mixture was concentrated under reduced pressure and partitioned between water and $CH_2Cl_2$. The organic layer was separated and dried over $Na_2SO_4$. After concentration, the crude product was purified by flash column chromatography (ethyl acetate/methanol) to produce $N^6$-Benzoyl-3'-O-(azidomethyl)-2'-deoxyadenosine (compound 2; FIG. 7) as a white powder (150 mg; 48% yield). $N^6$—Benzoyl-3'-O-(azidomethyl)-2'-deoxyadenosine (123 mg; 0.3 mmol) and a proton sponge (75.8 mg; 0.35 mmol) were then dried in a vacuum desiccator over $P_2O_5$ overnight before dissolving in trimethyl phosphate (600 μl). Next freshly distilled POCl3 (40 μl; 0.35 mmol) was added dropwise at 0° C. and the mixture was stirred at 0° C. for 2 h. Subsequently, a mixture of tributylammonium pyrophosphate (552 mg) and tributylamine (0.55 ml; 2.31 mmol) in anhydrous DMF (2.33 ml) was added at room temperature and stirred for 30 min. Triethyl ammonium bicarbonate solution (TEAB) (0.1 M; pH 8.0; 15 ml) was then added, and the mixture was stirred for 1 hour at room temperature. Subsequently, concentrated NH$_4$OH (15 ml) was added and stirred overnight at room temperature. The resulting mixture was concentrated under vacuum and the residue was diluted with 5 ml of water. The crude mixture was then purified with anion exchange chromatography on DEAE-Sephadex A-25 at 4° C. using a gradient of TEAB (pH 8.0; 0.1-1.0 M). The crude product was purified with reverse-phase HPLC to produce 3'-O-azidomethyl-dATP (FIG. 7, compound 3), a nucleotide analog to be used for later synthesis.

3'-O-azidomethyl-dTTP:

Acetic acid (4.8 ml) and acetic anhydride (15.4 ml) were added to a stirred solution of 5'-O-(tertbutyldimethylsilyl) thymidine (2.0 g; 5.6 mmol) [CNH Technologies, Woburn, Mass.] in DMSO. The reaction mixture was stirred at room temperature for 48 h. A saturated NaHCO$_3$ solution (100 ml) was added, and the aqueous layer was extracted with ethyl acetate (3×100 ml). The combined organic extract was washed with a saturated solution of NaHCO$_3$ and dried over Na$_2$SO$_4$. After concentration, the crude product was purified by flash column chromatography (hexane/ethyl acetate) to produce 3'-O-(Methylthiomethyl)-5'-O-(tert-butyldimethylsilyl)thymidine (FIG. 8; Compound 4) as a white powder (1.75 g; 75% yield). Approximately 1 gram of 3'-O-(Methylthiomethyl)-5'-O-(tert-butyldimethylsilyl)thymidine was then dissolved in dry CH$_2$Cl$_2$ (10 ml) under nitrogen. To this mixture cyclohexene (1.33 ml) and SO$_2$Cl$_2$ (284 µl; 3.5 mmol, redistilled) were added. The resulting mixture was then stirred at 0° C. for 1.5 h. The solvent was then removed under reduced pressure and then under high vacuum for 10 min. The residue was dissolved in dry DMF (5 ml) and reacted with NaN$_3$ (926 mg; 15.4 mmol) at room temperature for 3 h. That reaction mixture was next dispersed in distilled water (50 ml) and extracted with CH$_2$Cl$_2$ (3×50 ml). The combined organic extract was dried over Na$_2$SO$_4$ and concentrated under reduced pressure. The residue was dissolved in MeOH (5 ml) and reacted with NH$_4$F (600 mg; 16.2 mmol) at room temperature for 24 h. The reaction mixture was concentrated under reduced pressure and partitioned between water and CH$_2$Cl$_2$. The organic layer was then separated and dried over Na$_2$SO$_4$. After concentration, the residue was purified by flash column chromatography (hexane/ethyl acetate) to produce 3'-O-(azidomethyl)thymidine (FIG. 8, Compound 5) as a white powder (550 mg; 71% yield). Next, the 3'-O-(azidomethyl)thymidine and a proton sponge (0.35 mmol) were dried in a vacuum desiccator over P$_2$O$_5$ overnight before dissolving in trimethyl phosphate (600$_1$11). Next, freshly distilled POCl$_3$ (40$_1$11; 0.35 mmol) was added dropwise at 0° C. and the mixture was stirred at 0° C. for 2 h. Subsequently, a mixture of tributylammonium pyrophosphate (552 mg) and tributylamine (0.55 ml; 2.31 mmol) in anhydrous DMF (2.33 ml) was added at room temperature and stirred for 30 min. Triethyl ammonium bicarbonate solution (TEAB) (0.1 M; pH 8.0; 15 ml) was then added, and the mixture was stirred for 1 hour at room temperature. Subsequently, concentrated NH$_4$OH (15 ml) was added and stirred overnight at room temperature. The resulting mixture was concentrated under vacuum and the residue was diluted with 5 ml of water. The crude mixture was then purified with anion exchange chromatography on DEAE-Sephadex A-25 at 4° C. using a gradient of TEAB (pH 8.0; 0.1-1.0 M). The crude product was purified with reverse-phase HPLC to produce 3'-O-azidomethyl-dTTP (FIG. 8, compound 6), a nucleotide analog to be used for later synthesis.

3'-O-azidomethyl-dCTP:

Three and a half grams of N$^4$-benzoyl-5'-O-(tert-butyldimethylsilyl)-2'-deoxycytidine [CNH Technologies, Woburn, Mass.] was added to 14.7 ml of DMSO to produce a 7.65 mmol solution. To this solution, acetic acid (6.7 ml) and acetic anhydride (21.6 ml) were added, and the reaction mixture was stirred at room temperature for 48 h. A saturated NaHCO$_3$ solution (100 ml) was then added and the aqueous layer was extracted with CH$_2$Cl$_2$ (3×100 ml). The combined organic extract was washed with a saturated solution of NaHCO$_3$ and then dried over Na$_2$SO$_4$. After concentration, the crude product was purified by flash column chromatography (ethyl acetate/hexane) to produce N$^4$-Benzoyl-3'-O-(methylthiomethyl)-5'-O-(tert-butyldimethylsilyl)-2'-deoxycytidine (FIG. 9; compound 7) as a white powder (2.9 g; 73% yield). In 8 ml of CH$_2$Cl$_2$ N$^4$-Benzoyl-3'-O-(methylthiomethyl)-5'-O-(tert-butyldimethylsilyl)-2'-deoxycytidine (558 mg; 1.04 mmol) was dissolved and then cyclohexene (560$_1$11) and SO$_2$Cl$_2$ (220 µl; 2.7 mmol) were added. The reaction mixture was stirred at 0° C. for 1 h. The volatiles were then removed with reduced pressure. The remaining residue was dissolved in dry DMF (5 ml) and reacted with NaN$_3$ (400 mg; 6.6 mmol) at room temperature for 2 h. The reaction mixture was dispersed in distilled water (50 ml) and extracted with CH$_2$Cl$_2$ (3×50 ml). The combined organic extract was dried over Na$_2$SO$_4$ and concentrated under reduced pressure. The residue was dissolved in MeOH (5 ml) and reacted with NH$_4$F (600 mg; 16.2 mmol) at room temperature for 24 h. The solvent was removed under reduced pressure. The resulting residue was suspended in water (50 ml) and extracted with CH$_2$Cl$_2$ (3×50 ml). The combined organic extract was dried over Na$_2$SO$_4$ and concentrated under reduced pressure. The crude product was purified by flash column chromatography (hexane/ethyl acetate) to produce N$^4$-Benzoyl-3'-O-(azidomethyl)-2'-deoxycytidine (FIG. 9, compound 8) as a white powder (200 mg; 50% yield). Next, the N$^4$-Benzoyl-3'-O-(azidomethyl)-2'-deoxycytidine and a proton sponge (0.35 mmol) were dried in a vacuum desiccator over P$_2$O$_5$ overnight before dissolving in trimethyl phosphate (600 µl). Then freshly distilled POCl$_3$ (40$_1$11; 0.35 mmol) was added dropwise at 0° C. and the mixture was stirred at 0° C. for 2 h. Subsequently, a mixture of tributylammonium pyrophosphate (552 mg) and tributylamine (0.55 ml; 2.31 mmol) in anhydrous DMF (2.33 ml) was added at room temperature and stirred for 30 min. Triethyl ammonium bicarbonate solution (TEAB) (0.1 M; pH 8.0; 15 ml) was then added, and the mixture was stirred for 1 hour at room temperature. Subsequently, concentrated NH$_4$OH (15 ml) was added and stirred overnight at room temperature. The resulting mixture was concentrated under vacuum and the residue was diluted with 5 ml of water. The crude mixture was then purified with anion exchange chromatography on DEAE-Sephadex A-25 at 4° C. using a gradient of TEAB (pH 8.0; 0.1-1.0 M). The crude product was purified with reverse-phase HPLC to produce 3'-O-azidomethyl-dCTP (FIG. 9, compound 9), a nucleotide analog to be used for later synthesis.

3'-O-azidomethyl-dGTP:

To a stirred solution of N$^2$-isobutyryl-5'-O-(tert-butyldimethylsilyl)-2'-deoxyguanosine (5 g; 11.0 mmol) [CNH Technologies, Woburn, Mass.] in dry DMSO (21 ml), acetic acid (10 ml) and acetic anhydride (32 ml) were added. The reaction mixture was stirred at room temperature for 48 h. A saturated NaHCO$_3$ solution (100 ml) was added and the aqueous layer was extracted with ethyl acetate (3×100 ml). The combined organic extract was washed with a saturated NaHCO$_3$ solution and dried over Na$_2$SO$_4$. After concentration, the crude product was purified by flash column chromatography (CH$_2$Cl$_2$/MeOH) to produce N$^2$-Isobutyryl-3'-O-(methylthiomethyl)-5'-O-(tert-butyldimethylsilyl)-2'-deoxyguanosine (FIG. 10, compound 10) as a white powder (3.9 g; 69% yield). One gram of N$^2$-Isobutyryl-3'-O-(methylthiomethyl)-5'-O-(tert-butyldimethylsilyl)-2'-deoxyguanosine was subsequently added to dry pyridine (22 ml; 2.0 mmol) along with diphenylcarbamoyl chloride (677 mg; 2.92 mmol) and DIEA (N,N-diisopropylethylamine; SIGMA) (1.02 ml; 5.9 mmol). The reaction mixture was stirred under nitrogen atmosphere at room temperature for 3 h. The solvent was removed under high vacuum. The crude product was purified by flash column chromatography (ethyl acetate/hexane) to produce N$^2$-Isobutyryl-O$^6$-(diphenylcarbamoyl)-3'-O-(methylthiomethyl)-5'-O-(tert-butyldimethylsilyl)-2'-deoxyguanosine (FIG. 10, compound 11), which appeared as a yellowish powder (1.09 g; 80% yield). N$^2$—Isobutyryl-O$^6$-(diphenylcarbamoyl)-3'-O-(methylthiomethyl)-5'-O-(tert-butyldimethylsilyl)-2'-deoxyguanosine was then dissolved in dry CH$_2$Cl$_2$ (1.1 mmol) and stirred under nitrogen atmosphere at 0° C. for 1.5 h. The solvent was removed under reduced pressure and then under high vacuum for 10 min. The resulting residue was dissolved in dry DMF (5 ml) and reacted with NaN$_3$ (600 mg; 10 mmol) at room temperature for 3 h. The reaction mixture was then dispersed in distilled water (50 ml) and extracted with CH$_2$Cl$_2$(3×50 ml). The combined organic extract was dried over Na$_2$SO$_4$ and concentrated under reduced pressure. The resultant residue was dissolved in MeOH (5 ml) and reacted with NH$_4$F (500 mg; 13.5 mmol) at room temperature for 24 h. The solvent was removed under reduced pressure. The residue was suspended in water (50 ml) and extracted with CH$_2$Cl$_2$(3×50 ml). The combined organic extract was dried over Na$_2$SO$_4$ and concentrated under reduced pressure. The crude product was purified by flash column chromatography (hexane/ethyl acetate) to produce N$^2$-Isobutyryl-O$^6$-(diphenylcarbamoyl)-3'-O-azidomethyl-2'-deoxyguanosine (FIG. 10, compound 12) as a white powder (230 mg; 36% yield). Finally, the N$^2$-Isobutyryl-O$^6$-(diphenylcarbamoyl)-3'-O-azidomethyl-2'-deoxyguanosine and a proton sponge (0.35 mmol) were dried in a vacuum desiccator over P$_2$O$_5$ overnight before dissolving in trimethyl phosphate (600 µl). Then freshly distilled POC13 (40 µl; 0.35 mmol) was added dropwise at 0° C. and the mixture was stirred at 0° C. for 2 h. Subsequently, a mixture of tributylammonium pyrophosphate (552 mg) and tributylamine (0.55 ml; 2.31 mmol) in anhydrous DMF (2.33 ml) was added at room temperature and stirred for 30 min. Triethyl ammonium bicarbonate solution (TEAB) (0.1 M; pH 8.0; 15 ml) was then added, and the mixture was stirred for 1 hour at room temperature. Subsequently, concentrated NH$_4$OH (15 ml) was added and stirred overnight at room temperature. The resulting mixture was concentrated under vacuum and the residue was diluted with 5 ml of water. The crude mixture was then purified with anion exchange chromatography on DEAE-Sephadex A-25 at 4° C. using a gradient of TEAB (pH 8.0; 0.1-1.0 M). The crude product was purified with reverse-phase HPLC to produce 3'-O-azidomethyl-dGTP (FIG. 10, compound 13), a nucleotide analog to be used for later synthesis.

As described with respect to FIG. 2, once a 3'-O-blocked dNTP or 3'-O-blocked rNTP is added, it will be necessary to remove the blocking group so that additional dNTPs or rNTPs can be added. In some embodiments, the 3'-O-blocking group can be removed with a palladium catalyst in neutral aqueous solution at elevated temperature hydrochloric acid to pH 2, a reducing agent such as mercaptoethanol, or by the addition of tris-(2-carboxyethyl) phosphine. See, e.g., U.S. Pat. No. 6,664,079; Meng, et al. *J. Org. Chem.*, 2006, 71(81):3248-52; Bi et al., *J. Amer. Chem. Soc.* 2006; 2542-2543, U.S. Pat. Nos. 7,279,563, and 7,414,116, all of which are incorporated herein by reference in their entireties. In other embodiments, the 3'-substitution group may be removed by UV irradiation (see, e.g., WO 92/10587, incorporated by reference herein in its entirety). In some embodiments, the removal of the 3'-O-blocking group does not include chemical cleavage but uses a cleaving enzyme such as alkaline phosphatase.

3'-O-Methoxymethyl-dTTP:

5'-O-Benzoylthymidine (173 mg, 0.5 mmol, 1 equiv) was dissolved in 10 mL of dichloromethane under argon at ambient T. Di-isopropylethylamine (128 mg, 1 mmol, 2 equiv) was added followed by methoxymethyl bromide (124 mg, 1 mmol, 2 equiv). The mixture was stirred at ambient T for 18 h. The mixture was diluted with 10 mL dichloromethane and this was washed successively with 20 mL of 5% aq HCl, and brine. The organic layer was dried with sodium sulfate and evaporated. 5'-O-Benzoyl-3'-O-methoxymethylthymidine (50 mg, 0.13 mmol) was dissolved in 5 mL of concentrated ammonium hydroxide at ambient temperature. The mixture was stirred at ambient T overnight. The mixture was diluted extracted 3 times with 10 mL portions of dichloromethane. The combined extracts were washed with brine. The organic layer was dried with sodium sulfate and evaporated. 3'-O-Methoxymethylthymidine (23 mg, 0.08 mmol) was co-evaporated with pyridine (1.5 mL×3) and dried overnight under high vacuum. The nucleoside was dissolved in a mixture of 1.5 mL of trimethylphosphate and 0.6 mL dry pyridine under Ar. The mixture was cooled in an ice bath. a first aliquot of 10 uL of POC13 was added dropwise. Five minutes later, a second aliquot of 10 uL was added. The mixture was stirred an additional 30 min. A solution of the TBA phosphate salt in dry DMF (1.25 mL) was cooled in an ice bath in a vial under Ar. This was added to the rxn mixture dropwise over 10 sec. Immediately the pre-weighed solid proton sponge (21 mg, 1.25 equiv) was added as a solid in one portion. The mixture was stirred for 25 min after this addition and was quenched with 5 mL of cold TEAB buffer. The mixture was stirred in the ice bath for 10 min and then transferred to a small RB flask for FPLC separation. Final separation was accomplished by reverse phase HPLC using a water/acetonitrile gradient containing 0.1 mM formic acid.

3'-O-Methylthiomethyl-dCTP:

To a suspension of deoxycytidine (1 g, 4.4 mmol) in 25 mL of methanol was added N,N-dimethylformamide dimethyl acetal (1.75 mL, 13.2 mmol). The mixture was stirred overnight at ambient temperature. The reaction mixture was evaporated, and the residue was purified by flash chromatography using a DCM/methanol gradient as eluant. N6-Formamidino-5'-O-benzoyldeoxy-3'-O-methylthiomethyldeoxycytidine (250 mg, 0.41 mmol) was dissolved in 10 mL of methanol and 10 mL conc aqueous ammonium hydroxide. The mixture was stirred at ambient temperature for 18 h and then evaporated under reduced pressure. The residue was purified by column chromatography (DCM/Methanol 98:2 to 90:10) to afford 170 mg (93%) of the desired nucleoside as a slightly yellow solid. 3'-O-Methylthiomethyl dexoxycytidine (25.0 mg, 0.09 mmol) in a 25 mL vial was co-evaporated with anhydrous pyridine (3×1 mL) and dried over the weekend. Trimethyl phosphate (0.7 mL) was added to dissolve the nucleoside and cooled in an ice bath to 0° C. Phosphoryl chloride (28 µL, 0.3 mmol) was added slowly (12 µL, 5 min later 8 30 min later 8 µL) and the reaction was stirred for 2 h at 0° C. The di(tetrabutylammonium) hydrogen pyrophosphate was dissolved in anhydrous DMF (1 mL), this mixture was cooled to 0° C. and added to the reaction mixture. Proton sponge (9.2 mg, 0.04 mmol) was added and the reaction was stirred at 0° C. for 2 h. To the reaction mixture was added 1 M triethylammonium bicarbonate buffer (TEAB) (2 mL) and the mixture was stirred for 1 h. The mixture was then transferred to round-bottom flask, 50 mL×3 of miliQ water was added and mixture was concentrated to dryness. The residue was dissolved in miliQ water (11 mL) and loaded onto an AKTA FPLC at room temperature. The fractions containing the triphosphate (F48-F52) were evaporated under reduced pressure at 40° C., and the residue was then lyophilized. The triphosphate was dried to afford the desired triphosphate (12 mg, 16.5%).

EXAMPLES

Example 1: Protein Modifications

Murine (mur) TdT variants originated from 380 aa synthetic gene. This backbone is a truncated version of WT murine TdT and represents a catalytic core starting with amino acid XX and ending amino acid XXX of the ET sequence. Chemically synthesized TdT constructs were cloned into a pRSET A bacterial expression vector, featuring an N-terminal 6×-histidine tag and enterokinase cleavage site (ThermoFisher Scientific GeneArt Gene Synthesis). Synthetic TdT plasmids were maintained in DH5alpha cells (Biopioneer) plated on LB agar plates containing 100 ug/ml carbenicillin. For expression, the pRSETA-murine TdT plasmids were transformed into BL21 (DE3) pLysS cells (Thermo-Fisher) by incubating plasmids and cells on ice for 20 min., followed by a 30 sec. heat shock at 42° C., followed by addition of SOC media and incubation with shaking at 37° C. for 30-60 min. After addition of SOC media to cells, the entire volume (typically 60 ul) were plated on LB agar plates containing 100 ug/mL carbenicillin plus 34 ug/mL chloramphenicol.

Cells from 10 mL cultures (24-well plates, Corning) were harvested by centrifugation (3000×g, 15 min), then lysed in B-PER lysis buffer (Thermo-Fisher) containing lysozyme, protease inhibitors, and 100 mM NaCl. Pellets were soaked 1×60 min. in TBS buffer and supernatants collected for purification. The supernatant was bound onto 50 uL Ni-NTA bead (GE Life Sciences) slurry in 24-well plates for 30 min. The bead slurry was then washed 3×50 mM Tris-HCl, pH 8, 500 mM NaCl (500 uL), followed by washing 4×50 mM Tris-HCl, pH 8, 500 mM NaCl, 50 mM Imidazole (200 uL). The protein was then recovered by treating with 50 mM Tris-HCl, pH 8, 500 mM NaCl, 300 mM Imidazole (50 uL), then 50 mM Tris-HCl, pH 8, 500 mM NaCl, 300 mM Imidazole (130 uL), and finally 50 mM Tris-HCl, pH 8, 500 mM NaCl, 1M Imidazole (50 uL).

Recovered fractions were analyzed by taking 2.5 ul sample and running on 8% NuPage gel (Thermo-Fisher), 200 V for 50 min, denaturing conditions. Gel stained with Coomassie Blue. The eluted protein was buffer exchanged using a 7.5 MWCO desalting column (Thermo-Fisher) and sored at −80° C. (Storage Buffer=20 mM Tris-HCl, pH 6.8, 50 mM NaOAc; 0.01% Triton X-100 and 10% Glycerol).

Activity Screens:

TdT activity screening was performed via a dNTP polymerase extension reaction using different 3'-O-blocked dNTP analogs and a biotinylated oligonucleotide:

5BiosG/TAATAATAATAATAATAATAATAATAATAATAATAATTTTTT (ChemGenes Corporation)

Reactions were typically set up in a 96 well plate. Reactions were performed by making a master mix with final concentrations of the following components: 0.2 U PPase (Thermo-Fisher), 10 pmol of oligonucleotide, 75 uM dNTP (see below), 1×TdT reaction buffer (5× from Thermo-Fisher) to a final volume of 10 ul. Reactions were initiated by adding a defined volume (typically 2 ul) of TdT variants in different wells and incubating the reaction mix at 37° C. for 5 min and 60 min time points. Reactions were terminated by removal of a 10 ul aliquot and adding to 5 ul of 250 mM EDTA.

dNTPs Tested:
3'-O-azidomethyl-dTTP see description above
3'-O-azidomethyl-dATP see description above
3'-O-azidomethyl-dGTP see description above
3'-O-MOM-dTTP see description above
3'-O-MTM-dCTP see description above
3'-aminoxy-dTTP Firebird BioMolecular Sciences LLC
3'-aminoxy-dATP Firebird BioMolecular Sciences LLC
3'-aminoxy-dGTP Firebird BioMolecular Sciences LLC
3'-O-methyl-dATP TriLink BioTechnologies LLC
3'-O-methyl-dGTP TriLink BioTechnologies LLC
3'-O-methyl-dCTP TriLink BioTechnologies LLC Biotinylated oligos in the quenched reaction mix were bound to Streptavidin beads (0.77 um, Spherotech). The beads were then transferred to filter plates (Pall Corporation) and washed several times with water. The oligonucleotides were cleaved from the solid support by incubating the plate with cleavage buffer (10% Diisopropyl-amine in methanol) at 50° C. for 30 min followed by elution in water. The eluted samples were dried and dissolved in 30 ul water containing oligonucleotide sizing standards (two oligonucleotides (ChemGenes Corporation) that are approximately 15-20 bases smaller or larger than the starting 42-mer oligonucleotide). Oligonucleotides were then analyzed for extension efficiency by Capillary Gel Electrophoresis (Oligo Pro II, Advanced Analytical Technologies Inc.).

Example 2: In Silico Modeling

Several amino acid modifications to the GGFRR and TGSR motifs and flanking amino acids discussed above were modeled in silico to determine modifications capable of increased incorporation of 3'-O-blocked dNTP analogs as described above. Single, double, and triple amino acid substitutions as well amino acid insertions were modeled. Table 10 below shows modifications found to elicit increased incorporation. Amino acid positions are provided with reference to murine TdT but are applicable to conserved sequences of any TdT. Rows in Table 10 describe a base modification to one or more amino acids in or flanking the GGFRR motif. Columns include additional combinations of modifications to other amino acids such as those in and flanking the TGSR motif.

TABLE 10

| Residue Position | Single Site Mutation | Combination with E180K | Combination with R454T | Combination with E180K and R454T | Combination with R461V | Combination with N474R |
|---|---|---|---|---|---|---|
| T331 | T331M, T331S, T331A, T331V, T331G, T331I, T331N, T331C, T331L | T331M + E180K, T331S + E180K, T331A + E180K, T331V + E180K, T331G + E180K, T331I + E180K, T331N + E180K, T331C + E180K, T331L + E180K | T331M + R454T, T331S + R454T, T331A + R454T, T331V + R454T, T331G + R454T, T331I + R454T, T331N + R454T, T331C + R454T, T331L + R4541 | I331M + E180K + R454T, T331S + E180K + R454T, T331A + E180K + R454T, I331A + E180K + R454T, T331V + E180K + R454T, T331G + E180K + R454T, T331N + E180K + R454T, T331C + E180K + R454T, T331L + E180K + R454T | T331M + R461V, T331S + R461V, T331A + R461V, T331V + R461V, T331G + R461V, T331I + R461V, T331N + R461V, T331C + R461V, T331L + R461V | T331M + N474R, T331S + N474R, T331A + N474R, T331V + N474R, T331G + N474R, T331I + N474R, T331N + N474R, T331C + N474R, T331L + N474R |
| G332 | G332A | G332A + E180K | G332A + R454T | G332A + E180K + R4547 | G332A + R461V | G332A + N474R |
| G333 | G333S, G333A, G333D, G333P, G333E | G333S + E180K, G333A + E180K, G333D + E180K, G333P + E180K, G333E + E180K | G333S + R454T, G333A + R454T, G333D + R454T, G333P + R454T, G333E + R454T, | G333S + E180K + R454T, G333A + E180K + R454T, G333D + E180K + R454T, G333P + E180K + R454T, G333E + E180K + R454T | G333S + R461V, G333A + R461V, G333D + R461V, G333P + R461V, G333E + R461V | G333S + N474R, G333A + N474R, G333D + N474R, G333E + N474R, G333E + N474R |
| G333 and F334 | G333S + F334Y | G333S + F334Y + E180K | G333S + F334Y + R454T | G333S + F334Y + E180K + R454T | G333S + F334Y + R461V | G333S + F334Y + N474R |
| F334 | F334H, F334Y, F334N | F334H + E180K, F334Y + E180K, F334N + E180K | F334H + R454T, F334Y + R454T, F334N + R454T | F334H + E180K + R454T, F334Y + E180K + R454T, F334N + E180K + R454T | F334H + R461V, F334Y + R461V, F334N + R461V | F334H + N464R, F334Y + N474R, F334N + N474R |
| F334 and Y insertion between F334 and R335 | F334S + 334_335insY | F334S + 334_335insY + E180K | F334S + 334_335ins + Y + R454T | F334S + 334_335insY + E180K + R454T | F334S + 334_335insY + R461V | F334S + 334_335insY + N474R |
| R335 | R335L, R335S, R335K, R335W, R335T | R335L + E180K, R335S + E180K, R335K + E180K, R335W + E180K, R335T + E180K | R335L + R454T, R335S + R454T, R335K + R454T, R335W + R454T, R335T + R454T | R335L + E180K + R454T, R335S + E180K + R454T, R335K + E180K + R454T, R335W + E180K + R454T, | R335L + R461V, R335S + R461V, R335K + R461V, R335W + R461V, R335T + R461V | R335L + N474R, R335S + N474R, R335K + N474R, R335W + N474R, R335T + N474R |

TABLE 10-continued

| Residue Position | Single Site Mutation | Combination with E180K | Combination with R454T | Combination with E180K and R454T | Combination with R461V | Combination with N474R |
|---|---|---|---|---|---|---|
| R336 | R336K, R336S, R336I, R336N, R336V, R336Q | R336K + E180K, R336S + E180K, R336I + E180K, R336N + E180K, R336V + E180K, R336Q + E180K | R336S + R454T, R336S + R454T, R336I + R454T, R336N + R454T, R336V + R454T, R336Q + R454T | R335T + E180K + R454T, R336S + E180K + R454T, R336K + E180K + R454T, R336I + E180K + R454T, R336N + E180K + R454T, R336V + E180K + R454T, R336Q + E180K + R454T | R336K + R461V, R336S + R461V, R336I + R461V, R336N + R461V, R336V + R461V, R336Q + R461V | R336K + N474R, R336S + N474R, R336I + N474R, R336N + N474R, R336V + N474R, R336Q + N474R |
| G337 | G337K, G337E, G337A, G337D, G337H, G337S | G337K + E180K, G337E + E180K, G337A + E180K, G337D + E180K, G337H + E180K, G337S + E180K | G337E + R454T, G337E + R454T, G337A + R454T, G337D + R454T, G337H + R454T, G337H + R454T, G337S + R454T | R336S + E180K + R454T, R336S + E180K + R454T, G337A + E180K + R454T, G337D + R454T, R336I + E180K + R454T, R336N + E180K + R454T, R336I + E180K + R454T, R336V + E180K + R454T, R336Q + E180K + R454T | G337K + R461V, G337E + R461V, G337A + R461V, G337D + R461V, G337H + R461V, G337H + R461V, G337S + R461V | G337K + N474R, G337E + N474R, G337A + N474R, G337D + N474R, G337H + N474R, G337S + N474R |
| K338 | K338R, K338A | K338R + E180K, K338A + E180K | K338R + R454T, K338A + R454T | K338R + E180K + R454T, K338A + E180K + R454T | K338R + R461V, K338A + R461V | K338R + N474R, K338A + N474R |
| G341 | G341C, G341S, G341V, G341I | G341C + E180K, G341S + E180K, G341V + E180K, G341I + E180K | G341C + R454T, G341S + R454T, G341V + R454T, G341I + R454T | G341C + E180K + R454T, G341S + E180K + R454T, G341V + E180K + R454T, G341I + E180K + R454T | G341C + R461V, G341S + R461V, G341V + R461V, G341I + R461V | G341C + N474R, G341S + N464R, G341V + N474R, G341I + N474R |
| H342 | H342G, H342K, H342R, H342D | H342G + E180K, H342K + E180K, H342R + E180K, H342D + E180K | H342G + R454T, H342K + R454T, H342R + R454T, H342D + R454T | H342G + E180K + R454T, H342K + E180K + R454T, H342R + E180K + R454T, H342D + E180K + R454T | H342G + R461V, H342K + R461V, H342R + R461V, H342D + R461V | H342G + N474R, H342K + N474R, H342R + N474R, H342D + N474R |

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

---

What is claimed is:

1. A modified terminal deoxynucleotidyl transferase (TdT) comprising a mutation in a GGFRR amino acid motif and a TGSR amino acid motif, said modified TdT capable of adding a nucleotide analog comprising a removable 3'-O-blocking moiety to the 3'-OH of a nucleic acid initiator.

2. The modified TdT of claim 1, wherein the modified TdT is capable of adding the nucleotide analog comprising the removable 3'-O-blocking moiety to the 3'-OH of the nucleic acid initiator at an increased rate compared to native TdT.

3. The modified TdT of claim 1, wherein the modified TdT further comprises a mutation in a TGSR amino acid motif.

4. The modified TdT of claim 1, wherein the modified TdT comprises an N-terminus t-138 bovine TdT and a protein tag sequence fused to the N-terminus.

5. The modified TdT of claim 1, wherein the modified TdT comprises an N-terminus t-151 bovine TdT and a protein tag sequence fused to the N-terminus.

6. The modified TdT of claim 1, wherein the modified TdT comprises an N-terminus t-160 bovine TdT and a protein tag sequence fused to the N-terminus.

7. The modified TdT of claim 1, wherein the modified TdT is capable of adding adenine, cytosine, guanine, and thymine deoxyribonucleotides modified with a removable 3'-O-blocking moiety.

8. The modified TdT of claim 7, wherein said nucleotides are 2'-deoxyribonucleotides.

9. The modified TdT of claim 1, wherein the modified TdT is capable of adding adenine, cytosine, guanine, and uracil ribonucleotides modified with a removable 3'-O-blocking moiety.

10. The modified TdT of claim 1, wherein said removable 3'-O-blocking moiety comprises a 3'-O-azidomethyl group.

11. The modified TdT of claim 1, wherein said removable 3'-O-blocking moiety comprises a 3'-O-amino group.

12. The modified TdT of claim 1, wherein said removable 3'-O-blocking moiety comprises a 3'-O-allyl group.

13. The modified TdT of claim 1, wherein said removable 3'-O-blocking moiety is selected from the group consisting of O-phenoxyacetyl; O-methoxyacetyl; O-acetyl; O-(p-toluene)sulfonate; O-phosphate; O-nitrate; O-[4-methoxy]-tetrahydrothiopyranyl; O-tetrahydrothiopyranyl; O-[5-methyl]-tetrahydrofuranyl; O-[2-methyl,4-methoxy]-tetrahydropyranyl; O-[5-methyl]-tetrahydropyranyl; and O-tetrahydrothiofuranyl.

14. The modified TdT of claim 1, wherein the modified TdT is capable of incorporating a 3'-O-blocked nucleotide 5'-triphosphate, and said removable blocking moiety comprises a group selected from esters, ethers, carbonitriles, phosphates, carbonates, carbamates, hydroxylamine, borates, nitrates, sugars, phosphoramide, phosphoramidates, phenylsulfenates, sulfates, sulfones and amino acids.

15. The modified TdT of claim 1, wherein the modified TdT is capable of incorporating modified nucleotides at a reaction temperature of about 30° C.

16. The modified TdT of claim 1, wherein the modified TdT is capable of incorporating modified nucleotides at a reaction temperature from 30° C. to 80° C.

17. The modified TdT of claim 1, wherein the modified TdT is capable of incorporating modified nucleotides at a concentration of 1000 µM or less.

18. The modified TdT of claim 17, wherein the modified TdT is capable of incorporating modified nucleotides at a concentration of 100 µM or less.

19. The modified TdT of claim 1, wherein the modified TdT is expressed by an organism having a genome comprising a nucleic acid sequence being at least 90% identical to SEQ ID NOS. 2, 4, 6, or 8.

20. The modified TdT of claim 1, wherein the GGFRR motif comprises a mutation selected from G, A, V, L, I, M, F, W, P, S, T, C, Y, N, Q, D, E, K, R, or H.

* * * * *